United States Patent
Xu et al.

(10) Patent No.: US 12,227,707 B2
(45) Date of Patent: *Feb. 18, 2025

(54) METHODS FOR PROCESSING A HYDROCARBON OIL FEED STREAM UTILIZING A GASIFICATION UNIT, STEAM ENHANCED CATALYTIC CRACKER, AND AN AROMATICS COMPLEX

(71) Applicant: Saudi Arabian Oil Company, Dhahran (SA)

(72) Inventors: Qi Xu, Dhahran (SA); Aaron Chi Akah, Dhahran (SA); Musaed Salem Al-Ghrami, Dammam (SA); Zhonglin Zhang, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/865,995

(22) Filed: Jul. 15, 2022

(65) Prior Publication Data
US 2024/0018432 A1    Jan. 18, 2024

(51) Int. Cl.
*C10G 11/20* (2006.01)
*C01B 3/24* (2006.01)
(Continued)

(52) U.S. Cl.
CPC ............... *C10G 69/14* (2013.01); *C01B 3/24* (2013.01); *C07C 6/126* (2013.01); *C10G 9/36* (2013.01);
(Continued)

(58) Field of Classification Search
CPC .......... C10G 69/14; C10G 9/36; C10G 11/20; C10G 21/003; C10G 35/04; C10G 49/22;
(Continued)

(56) References Cited

U.S. PATENT DOCUMENTS 2,416,023 A * 2/1947 Helmers ................. C10G 11/20
585/407
3,361,535 A * 1/1968 Pollitzer ..................... C01B 3/38
585/934
(Continued)

FOREIGN PATENT DOCUMENTS

EP      3578623 A1    12/2019
WO   2009003634 A1    1/2009
(Continued)

OTHER PUBLICATIONS

Akah et al., "An Overview of Light Olefins Production via Steam Enhanced Catalytic Cracking", Catalysis Surveys from Asia, vol. 23, pp. 265-276, 2019.
(Continued)

*Primary Examiner* — Michelle Stein
(74) *Attorney, Agent, or Firm* — DINSMORE & SHOHL LLP

(57) ABSTRACT

In accordance with one or more embodiments herein, an integrated process for upgrading a hydrocarbon oil feed stream utilizing a gasification unit, steam enhanced catalytic cracker, and an aromatics complex includes solvent deasphalting the hydrocarbon oil stream; processing the heavy residual hydrocarbons in a gasification unit to form syngas and gasification residue; hydrotreating the deasphalted oil stream to form a light $C_{5+}$ hydrocarbon stream and a heavy $C_{5+}$ hydrocarbon stream; steam enhanced catalytically cracking the light $C_{5+}$ hydrocarbon stream; steam enhanced catalytically cracking the heavy $C_{5+}$ hydrocarbon stream; passing at least a portion of the light steam enhanced catalytically cracked stream, the heavy steam enhanced catalytically cracked stream, or both to a product separator to produce a olefin product stream, a naphtha product stream, and a BTX product stream; and processing the
(Continued)

naphtha product stream in the aromatics complex to produce benzene and xylenes.

12 Claims, 2 Drawing Sheets

(51) Int. Cl.
| | |
|---|---|
| *C07C 6/12* | (2006.01) |
| *C10G 9/36* | (2006.01) |
| *C10G 21/00* | (2006.01) |
| *C10G 35/04* | (2006.01) |
| *C10G 49/22* | (2006.01) |
| *C10G 69/14* | (2006.01) |
| *C10J 3/00* | (2006.01) |

(52) U.S. Cl.
CPC ............ *C10G 11/20* (2013.01); *C10G 21/003* (2013.01); *C10G 35/04* (2013.01); *C10G 49/22* (2013.01); *C10J 3/00* (2013.01); *C01B 2203/065* (2013.01); *C01B 2203/1241* (2013.01); *C10G 2300/1033* (2013.01); *C10G 2300/301* (2013.01); *C10G 2300/4006* (2013.01); *C10G 2300/4012* (2013.01); *C10G 2300/4018* (2013.01); *C10G 2300/4081* (2013.01); *C10G 2300/42* (2013.01); *C10G 2400/20* (2013.01); *C10G 2400/30* (2013.01); *C10J 2300/16* (2013.01)

(58) Field of Classification Search
CPC ...... C10G 2300/301; C10G 2300/4006; C10G 2300/4012; C07C 6/126; C10J 3/00
See application file for complete search history.

(56) References Cited

U.S. PATENT DOCUMENTS

| | | | | |
|---|---|---|---|---|
| 3,702,292 | A * | 11/1972 | Burich | C10G 69/10 422/139 |
| 3,775,293 | A | 11/1973 | Watkins | |
| 3,784,463 | A * | 1/1974 | Reynolds | C10G 11/18 208/77 |
| 4,111,793 | A * | 9/1978 | Kolombos | C10G 11/10 585/653 |
| 6,660,158 | B1 * | 12/2003 | Ellingsen | C10G 11/18 208/158 |
| 6,740,788 | B1 * | 5/2004 | Maher | C07C 6/126 585/475 |
| 7,491,315 | B2 | 2/2009 | Eng et al. | |
| 8,631,311 | B1 | 1/2014 | Chan et al. | |
| 8,685,232 | B2 | 4/2014 | Mandal et al. | |
| 9,228,140 | B2 | 1/2016 | Abba et al. | |
| 10,316,258 | B2 | 6/2019 | Rispoli et al. | |
| 10,407,630 | B2 | 9/2019 | Al-Ghamdi et al. | |
| 10,472,580 | B2 | 11/2019 | Al-Ghamdi et al. | |
| 10,717,941 | B2 | 7/2020 | Al-Ghamdi et al. | |
| 11,230,673 | B1 * | 1/2022 | Al-Ghrami | C10G 51/06 |
| 11,242,493 | B1 | 2/2022 | Xu et al. | |
| 11,332,680 | B2 * | 5/2022 | Al-Ghrami | C10G 47/30 |
| 11,352,575 | B2 * | 6/2022 | Al-Ghrami | C10G 11/18 |
| 11,370,975 | B2 * | 6/2022 | Akah | C10G 11/05 |
| 11,851,622 | B1 * | 12/2023 | Akah | C10J 3/00 |
| 2006/0042999 | A1 * | 3/2006 | Iqbal | C10G 9/005 208/309 |
| 2008/0223754 | A1 * | 9/2008 | Subramanian | C10G 69/04 196/14.52 |
| 2009/0143631 | A1 * | 6/2009 | Gracey | C10G 27/04 585/650 |
| 2009/0294328 | A1 * | 12/2009 | Iqbal | C10G 51/06 208/67 |
| 2010/0037909 | A1 * | 2/2010 | Gross | A61K 8/4953 8/409 |
| 2010/0317909 | A1 | 12/2010 | Keyvanloo et al. | |
| 2013/0112593 | A1 * | 5/2013 | Montanari | C10G 67/049 208/57 |
| 2013/0248419 | A1 * | 9/2013 | Abba | C10G 69/00 208/67 |
| 2013/0248421 | A1 * | 9/2013 | Abba | C10G 11/18 208/80 |
| 2014/0110308 | A1 * | 4/2014 | Bourane | C10G 51/06 208/80 |
| 2016/0369189 | A1 | 12/2016 | Ward et al. | |
| 2018/0142167 | A1 * | 5/2018 | Al-Ghamdi | C10G 47/02 |
| 2018/0155633 | A1 * | 6/2018 | Al-Ghamdi | C10G 9/005 |
| 2018/0291288 | A1 | 10/2018 | Brown et al. | |
| 2018/0305623 | A1 * | 10/2018 | Al-Ghrami | C10G 51/06 |
| 2018/0346827 | A1 * | 12/2018 | Al-Ghamdi | C10G 7/00 |
| 2019/0225894 | A1 * | 7/2019 | Bourane | B01J 8/003 |
| 2020/0115645 | A1 | 4/2020 | Al-Ghamdi et al. | |
| 2020/0392055 | A1 * | 12/2020 | Nesterenko | C10G 51/04 |
| 2021/0040398 | A1 * | 2/2021 | Al-Ghamdi | B01J 8/26 |
| 2021/0087476 | A1 | 3/2021 | Boualleg et al. | |
| 2021/0139793 | A1 * | 5/2021 | Al-Shafei | C10G 11/05 |
| 2022/0017829 | A1 | 1/2022 | Al-Shafei et al. | |
| 2022/0064546 | A1 * | 3/2022 | Al-Ghrami | C10G 47/30 |
| 2022/0064548 | A1 * | 3/2022 | Akah | C10G 11/05 |
| 2022/0064556 | A1 * | 3/2022 | Akah | B01J 19/2445 |

FOREIGN PATENT DOCUMENTS

| | | |
|---|---|---|
| WO | 2015128040 A1 | 9/2015 |
| WO | 2017023611 A1 | 2/2017 |

OTHER PUBLICATIONS

U.S. Office Action dated Mar. 27, 2023 pertaining to U.S. Appl. No. 17/866,029, filed Jul. 15, 2022, pp. 1-22.
U.S. Office Action dated Mar. 27, 2023 pertaining to U.S. Appl. No. 17/866,035, filed Jul. 15, 2022, pp. 1-21.
US Office Action dated Apr. 14, 2023 pertaining to U.S. Appl. No. 17/865,787, filed Jul. 15, 2022, pp. 1-24.
Notification of Transmittal of the International Search Report and the Written Opinion of the International Searching Authority, or the Declaration dated Oct. 6, 2023 pertaining to International application No. PCT/US2023/070023 filed Jul. 12, 2023, pp. 1-18.
Notification of Transmittal of the International Search Report and the Written Opinion of the International Searching Authority, or the Declaration dated Oct. 10, 2023 pertaining to International application No. PCT/US2023/070024 filed Jul. 12, 2023, pp. 1-18.
Wu, Wei "Advances and Development of Aromatics Production Technologies for an Aromatics Complex", Acta Petrolei Sinica, vol. 31, No. 2, Jan. 1, 2015, pp. 275-281.

* cited by examiner

METHODS FOR PROCESSING A HYDROCARBON OIL FEED STREAM UTILIZING A GASIFICATION UNIT, STEAM ENHANCED CATALYTIC CRACKER, AND AN AROMATICS COMPLEX

TECHNICAL FIELD

Embodiments of the present disclosure generally relate to refining and upgrading hydrocarbon oil, and pertain particularly to an integrated process and system for upgrading a hydrocarbon oil stream, including heavy hydrocarbon residuals.

BACKGROUND

Olefins and aromatic compounds, such as ethylene, propylene, butylene, butadiene, benzene, toluene, and xylenes, are basic intermediates for many petrochemical industries. These olefins and aromatic compounds are usually obtained through the thermal cracking (or steam pyrolysis) of petroleum gases and distillates such as naphtha, kerosene, or gas oil. These compounds are also produced through refinery fluidized catalytic cracking (FCC) process where standard heavy feedstocks, such as gas oils or residues, are converted. Typical FCC feedstocks range from hydrocracked bottoms to heavy feed fractions, such as vacuum gas oil and atmospheric residue. However, these feedstocks are limited. Another source for propylene production is currently refinery propylene from FCC units. With the ever-growing demand, FCC unit owners look increasingly to the petrochemicals market to boost their revenues by taking advantage of economic opportunities that arise in the propylene market.

The worldwide increasing demand for light olefins remains a major challenge for many integrated refineries. In particular, the production of some valuable light olefins such as ethylene, propylene, and butylene has attracted increased attention as pure olefin streams are considered the building blocks for polymer synthesis. The production of light olefins depends on several process variables like the feed type, operating conditions, and the type of catalyst.

SUMMARY

Despite the options available for producing a greater yield of propylene and other light olefins, intense research activity in this field is still being conducted. It is desirable to produce light olefins and/or benzene, toluene, and xylenes, collectively referred to as "BTX," directly from a crude oil source. However, such methods may be problematic since crude oils often contain heavy residual hydrocarbons and other impurities that may interfere with the refining process, for example, in hydrocracking, steam cracking, and fluid catalytic cracking.

For example, these heavy residual hydrocarbons, such as asphaltenes, may affect the previous processes by generating a large amount of petroleum coke on catalysts used in the said refining processes. This buildup of coke may deactivate the catalysts used, resulting in increased costs to recycle or replace said deactivated catalysts or lowered light olefin/BTX conversion rates. The impurities may also negatively impact the said refining processes by lowering their efficiencies. The negative effects of nitrogen as an impurity in refining processes is well-known, contributing to a variety of problems such as, but not limited to, gum formation, catalyst inhibition and deactivation, acid-base pair-related corrosion, metal complexation, or combinations thereof.

Therefore, it may be desirable to initially treat a crude oil stream to upgrade heavy residual hydrocarbons and remove impurities and heavy residual hydrocarbons before the crude oil stream is refined to avoid these negative effects.

Described herein are integrated processes and systems for producing light olefins (e.g., $C_2$-$C_4$ olefins) and/or BTX from crude oils, while providing the aforementioned benefits. Heavy hydrocarbons residuals such as asphaltenes may be processed in a solvent deasphalting unit and gasification unit to produce a deasphalted oil stream, syngas, and gasification residue. The deasphalted oil stream may be further upgradable to light olefins and BTX. The crude oil fractions, as the deasphalted oil stream, may be refined in a hydrotreater and separated into at least four fractions, which are separately processed. $C_{5+}$ hydrocarbon fractions may then be processed in steam-enhanced catalytic crackers to produce light olefins, naphtha, and BTX. The naphtha may then be processed in an aromatics complex to produce primarily benzene and xylenes as BTX. In this way, the entire crude oil is utilized to produce at least syngas, olefins, BTX, gasification residue, and petroleum coke.

In accordance with one embodiment herein, an integrated process for upgrading a hydrocarbon oil feed stream includes solvent deasphalting a hydrocarbon oil stream to form at least a deasphalted oil stream and heavy residual hydrocarbons, the heavy residual hydrocarbons including at least asphaltenes; processing the heavy residual hydrocarbons in a gasification unit to produce syngas and gasification residue; hydrotreating the deasphalted oil stream to produce a light $C_{5+}$ hydrocarbon stream and a heavy $C_{5+}$ hydrocarbon stream; steam enhanced catalytically cracking the light $C_{5+}$ hydrocarbon stream to form a light steam enhanced catalytically cracked product including olefins, BTX, naphtha, or combinations thereof; steam enhanced catalytically cracking the heavy $C_{5+}$ hydrocarbon stream to form a heavy steam enhanced catalytically cracked product comprising olefins, BTX, naphtha, or combinations thereof; passing at least a portion of the light steam enhanced catalytically cracked stream, the heavy steam enhanced catalytically cracked stream, or both to a product separator to produce a olefin product stream, a naphtha product stream, and a BTX product stream; and processing naphtha product stream in an aromatics complex to produce benzene and xylenes.

According to another embodiment herein, an integrated system for the conversion of hydrocarbon oil feed streams includes a solvent deasphalting unit that separates a hydrocarbon oil stream into at least a deasphalted oil stream and heavy residual hydrocarbons, the heavy residual hydrocarbons including at least asphaltenes; a gasification unit fluidly connected to the solvent deasphalting unit that processes the heavy residual hydrocarbons to form syngas and gasification residue; a hydrotreater fluidly connected to the solvent deasphalting unit that hydrotreats at least the deasphalted oil stream to form a light $C_{5+}$ hydrocarbon stream and a heavy $C_{5+}$ hydrocarbon stream; a first steam-enhanced catalytic cracker fluidly connected to the hydrotreater that cracks at least a portion of the light $C_{5+}$ hydrocarbon fraction to form a light steam enhanced catalytically cracked product; a second steam-enhanced catalytic cracker fluidly connected to the hydrotreater that cracks at least a portion of the heavy $C_{5+}$ hydrocarbon fraction to form a heavy steam enhanced catalytically cracked product; a product separator fluidly connected to the first and second steam enhanced catalytic crackers that produces an olefin product stream, a naphtha product stream, and a BTX product stream; and an aromatics complex fluidly connected to the product separator that processes the naphtha product stream to produce benzene and xylenes.

Additional features and advantages of the embodiments described herein will be set forth in the detailed description which follows, and in part will be readily apparent to those skilled in the art from that description or recognized by practicing the embodiments described, including the detailed description and the claims which are provided infra.

BRIEF DESCRIPTION OF THE DRAWINGS

The following detailed description of specific embodiments of the present disclosure can be best understood when read in conjunction with the following drawings in which.

Figure 1:
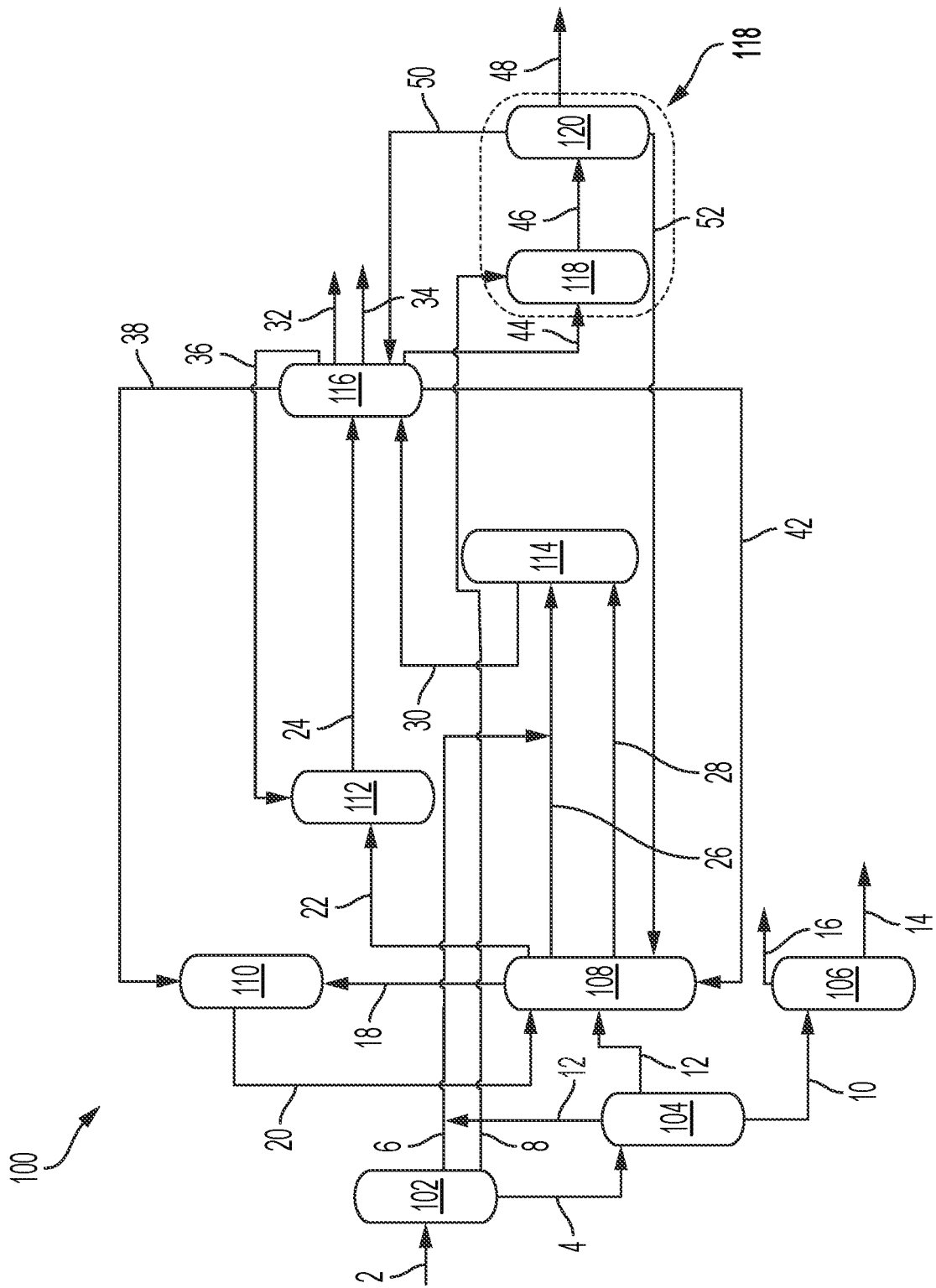
FIG. 1 illustrates a process flow diagram for an exemplary process in accordance with embodiments described herein.

For the purpose of describing the simplified schematic illustrations and descriptions of the relevant figures, the numerous valves, temperature sensors, electronic controllers and the like that may be employed and well known to those of ordinary skill in the art of certain chemical processing operations are not included. Further, accompanying components that are often included in typical chemical processing operations, such as air supplies, catalyst hoppers, and flue gas handling systems, are not depicted. Accompanying components that are in hydrotreating units, such as bleed streams, spent catalyst discharge subsystems, and catalyst replacement sub-systems are also not shown. It should be understood that these components are within the spirit and scope of the present embodiments disclosed. However, operational components, such as those described in the present disclosure, may be added to the embodiments described in this disclosure.

It should further be noted that arrows in the drawings refer to process streams. However, the arrows may equivalently refer to transfer lines, which may serve to transfer process streams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows, which do not connect two or more system components, signify a product stream, which exits the depicted system, or a system inlet stream, which enters the depicted system. Product streams may be further processed in accompanying chemical processing systems or may be commercialized as end products. System inlet streams may be streams transferred from accompanying chemical processing systems or may be non-processed feedstock streams. Some arrows may represent recycle streams, which are effluent streams of system components that are recycled back into the system. However, it should be understood that any represented recycle stream, in some embodiments, may be replaced by a system inlet stream of the same material, and that a portion of a recycle stream may exit the system as a product.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that according to the embodiments presented in the relevant figures, an arrow between two system components may signify that the stream is not processed between the two system components. In other embodiments, the stream signified by the arrow may have substantially the same composition throughout its transport between the two system components. Additionally, it should be understood that in embodiments, an arrow may represent that at least 75 wt. %, at least 90 wt. %, at least 95 wt. %, at least 99 wt. %, at least 99.9 wt. %, or even 100 wt. % of the stream is transported between the system components. As such, in embodiments, less than all of the stream signified by an arrow may be transported between the system components, such as if a slip stream is present.

It should be understood that two or more process streams are "mixed" or "combined" when two or more lines intersect in the schematic flow diagrams of the relevant figures. Mixing or combining may also include mixing by directly introducing both streams into a like reactor, separation unit, or other system component. For example, it should be understood that when two streams are depicted as being combined directly prior to entering a separation unit or reactor, that in embodiments the streams could equivalently be introduced into the separation unit or reactor and be mixed in the reactor. Alternatively, when two streams are depicted to independently enter a system component, they may in embodiments be mixed together before entering that system component.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments of the present disclosure are directed to integrated processes and systems for producing light olefins (e.g., $C_2$-$C_4$ olefins) and/or BTX from crude oils, while providing the aforementioned benefits.

As used herein, "asphaltenes" refers generally to the heaviest and most polar compounds naturally occurring in crude oil. Asphaltenes are a mixture of high molecular weight polycyclic aromatic hydrocarbons and heterocyclic compounds, primarily comprising carbon, hydrogen, nitrogen, oxygen, and sulfur, as well as trace amounts of vanadium and nickel. In asphaltenes, the hydrogen-to-carbon atomic ratio is approximately 1.2:1.0. Asphaltenes are generally n-pentane or n-heptane-insoluble, but toluene-soluble, and are generally a sticky, black, highly viscous residue of distillation processes.

As used herein, a "catalyst" refers to any substance that increases the rate of a specific chemical reaction. Catalysts described in this disclosure may be utilized to promote various reactions, such as, but not limited to, cracking (including aromatic cracking), demetalization, desulfurization, and denitrogenation. As used herein, "cracking" generally refers to a chemical reaction where carbon-carbon bonds are broken. For example, a molecule having carbon to carbon bonds is broken into more than one molecule by the breaking of one or more of the carbon to carbon bonds, or is converted from a compound which includes a cyclic moiety, such as a cycloalkane, cycloalkane, naphthalene, an aromatic or the like, to a compound which does not include a cyclic moiety or contains fewer cyclic moieties than prior to cracking.

As used herein, "catalytic reforming" refers to a conversion process in petroleum refining and petrochemical industries. The reforming process generally catalytically converts low octane naphtha distilled from crude oil into higher octane reformate that contains aromatic compounds with a high amount of BTX. Generally, there are four major types of reactions taking place during reforming processes: (1) dehydrogenation of naphthenes to aromatics; (2) dehydrocyclization of paraffins to aromatics; (3) isomerization; and (4) hydrocracking.

As used herein, the term "crude oil" is to be understood to mean a mixture of petroleum liquids, gases, or combinations of liquids and gases, including some impurities such as sulfur-containing compounds, nitrogen-containing compounds and metal compounds that have not undergone significant separation or reaction processes. Crude oils are distinguished from fractions of crude oil. As used herein, the crude oil may be a minimally treated crude oil to provide a hydrocarbon oil feedstock having total metals (Nickel+ Vanadium) content of less than 5 parts per million by weight (ppmw) and Conradson carbon residue of less than 5 wt. % Such minimally treated materials may be considered crude oils as described herein.

As used herein, "distillate" refers to a crude oil fraction that includes $C_{5+}$ hydrocarbons with boiling points of between 204° C. and 343° C. Distillate may also be primarily composed of diesel and kerosene.

It should be understood that an "effluent" generally refers to a stream that exits a system component such as a separation unit, a reactor, or reaction zone, following a particular reaction or separation, and generally has a different composition (at least proportionally) than the stream that entered the separation unit, reactor, or reaction zone.

As used herein, "heavy cycle oil" refers to a hydrocarbon crude oil fraction that includes $C_{5+}$ hydrocarbons with boiling points of between 426° C. and 640° C. "Light cycle oil," as used herein, refers to a crude oil fraction that includes $C_{5+}$ hydrocarbons with boiling points of between 343° C. and 426° C.

As used herein, the terms "hourly space velocity," "gas hourly space velocity," and "liquid hourly space velocity" may collectively refer to the rate at which a feed stream travels through the treatment units, reactors, and separators discussed herein. Further, hourly space velocity may also be inversely proportional to the residence time for the same, i.e. residence time may be expressed as one over the hourly space velocity. "Residence time," as used herein, refers to the amount of time taken for a feed stream to enter and then exit the treatment units, reactors, and separators discussed herein.

As used herein, the term "naphtha" refers to a mixture of substances primarily including $C_5$ to $C_{11}$ hydrocarbons. "Light naphtha," as used herein, is a fraction of naphtha primarily including $C_5$ to $C_6$ hydrocarbons. As used herein, the term "heavy naphtha" refers to a fraction of naphtha primarily including $C_7$ to $C_{11}$ hydrocarbons.

As used herein, the term "steam/oil ratio" or "steam-to-oil ratio" or "steam-to-hydrocarbon oil ratio" or "steam-to-feed ratio" refers to a standard measure of the volume rate of steam circulating through the reactor with respect to the volume of feed. The steam/oil ratio may be determined by comparing the flow volume of a steam stream and the flow volume of a hydrocarbon oil feed or the flow volume of a second steam stream and the flow volume of a hydrocarbon product stream.

As used herein, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Exemplary reactors include packed bed reactors such as fixed-bed reactors, and fluidized bed reactors. One or more "reaction zones" may be disposed in a reactor. As used herein, a "reaction zone" refers to an area where a particular reaction takes place in a reactor. For example, a packed bed reactor with multiple catalyst beds may have multiple reaction zones, where each reaction zone is defined by the area of each catalyst bed.

As used herein, a "separation unit" or "separator" refers to any separation device that at least partially separates one or more chemicals that are mixed in a process stream from one another. For example, a separation unit may selectively separate differing chemical species, phases, or sized material from one another, forming one or more chemical fractions. Examples of separation units include, without limitation, distillation columns, flash drums, knock-out drums, knock-out pots, centrifuges, cyclones, filtration devices, traps, scrubbers, expansion devices, membranes, solvent extraction devices, and the like. It should be understood that separation processes described in this disclosure may not completely separate all of one chemical constituent from all of another chemical constituent. It should be understood that the separation processes described in this disclosure "at least partially" separate different chemical components from one another, and that even if not explicitly stated, it should be understood that separation may include only partial separation. As used herein, one or more chemical constituents may be "separated" from a process stream to form a new process stream. Generally, a process stream may enter a separation unit and be divided, or separated, into two or more process streams of desired composition. Further, in some separation processes, a "lower boiling point fraction" (sometimes referred to as a "light fraction" or "light fraction stream") and a "higher boiling point fraction" (sometimes referred to as a "heavy fraction," "heavy hydrocarbon fraction," or "heavy hydrocarbon fraction stream") may exit the separation unit, where, on average, the contents of the lower boiling point fraction stream have a lower boiling point than the higher boiling point fraction stream. Other streams may fall between the lower boiling point fraction and the higher boiling point fraction, such as a "medium boiling point fraction."

It should further be understood that streams may be named for the components of the stream, and the component for which the stream is named may be the major component of the stream (such as comprising from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. By way of non-limiting example, a referenced "$C_2$-$C_4$ hydrocarbon stream" passing from a first system component to a second system component should be understood to equivalently disclose "$C_2$-$C_4$ hydrocarbons" passing from a first system component to a second system component, and the like.

Referring initially to FIG. 1, an integrated system 100 for the conversion of hydrocarbon oil feedstocks is illustrated. As used herein, "feed stock" may also be used to refer to "feed stream(s)." The integrated system 100 includes a solvent deasphalting unit 104, a gasification unit 106, a hydrotreater 108, steam enhanced catalytic crackers 114, a product separator, and an aromatics complex 118. While FIG. 1 appears to show only one steam enhanced catalytic cracker, it should be understood that 114 is meant to illustrate multiple steam enhanced catalytic crackers, particularly a first steam enhanced catalytic cracker and a second steam enhanced catalytic cracker, together encompassing the steam enhanced catalytic crackers 114. The illustration of one steam enhanced catalytic cracker for 114 is meant for simplification of the flow patterns of FIG. 1.

Further, it should be understood that the use of "light" and "heavy" as identifiers for the steam enhanced catalytic crackers 114 are used simply for the purpose of referencing the feed streams that may enter the steam enhanced catalytic crackers 114. For example, the light steam enhanced catalytic cracker may be understood to have lighter hydrocarbon feeds that have lower boiling points than the feeds for heavy steam enhanced catalytic cracker. Similarly, the heavy steam enhanced catalytic cracker may be understood to have heavier hydrocarbon feeds that have higher boiling points than the feeds for the light steam enhanced catalytic cracker.

Still referring to FIG. 1, the solvent deasphalting unit 104 may separate a hydrocarbon oil stream 2 into at least a deasphalted oil stream 12 and heavy residual hydrocarbons 10. The heavy residual hydrocarbons 10 may include at least asphaltenes in the form of a pitch. In embodiments, the solvent deasphalting unit may include a solvent. The solvent may be a light paraffinic hydrocarbon, such as, but not limited to n-propane, n-butane, n-pentane, n-hexane, n-heptane, or combinations thereof. The gasification unit 106 is fluidly connected to the solvent deasphalting unit 104 and processes the heavy residual hydrocarbons 10 to form syngas 16 and gasification residue 14. In embodiments, the heavy residual hydrocarbons 10 may further include non-hydrocarbon constituents and impurities. In this way, the solvent deasphalting unit 104 may remove asphaltenes, non-hydrocarbon constituents, impurities, or combinations thereof, from the hydrocarbon oil stream 2 to form the deasphalted oil stream 10. For example, the solvent deasphalting unit 104 may remove nitrogen-containing compounds, sulfur-containing compounds, Conradson carbon residue (CCR), and metal compounds such as nickel and vanadium. In embodiments, removing non-hydrocarbon constituents and impurities like the immediately previous may increase the efficiency of downstream treatment units by reducing the coking deactivation rate of the various catalysts used therein.

In embodiments, the solvent deasphalting unit 104 may be operated at a temperature of from 40° C. to 100° C., from 40° C. to 90° C., from 40° C. to 70° C., from 40° C. to 60° C., from 60° C. to 100° C., from 60° C. to 90° C., from 60° C. to 70° C., from 70° C. to 100° C., from 70° C. to 90° C., or from 90° C. to 100° C. The solvent deasphalting unit 104 may be operated at a pressure of from 0.1 MPa to 0.4 MPa.

In embodiments, processing the heavy residual hydrocarbons 10 in the gasification unit 106 may include exposing the heavy residual hydrocarbons to air at elevated temperatures and pressures to convert the heavy residual hydrocarbons into the syngas 16 and the gasification residue 14. In embodiments, the gasification unit 106 may be operated at a temperature of less than or equal to 1100° C., less than or equal to 900° C., less than or equal to 600° C., or even less than or equal to 400° C. The gasification unit 106 may be operated at a temperature of from 400° C. to 1100° C., from 400° C. to 900° C., from 400° C. to 600° C., from 600° C. to 1100° C., from 600° C. to 900° C., or from 900° C. to 1100° C. The gasification unit 106 may be operated at a pressure of from 0.1 MPa to 6.2 MPa. The gasification unit 106 may also be operated at a pressure of from 1 MPa to 6.2 MPa. In embodiments, the gasification unit 106 may also be operated in a low oxygen environment, such as less than 10 mol. %, less than 5 mol. %, less than 2.5 mol. %, less than 1 mol. %, less than 0.5 mol. %, or even less than 0.1 mol. % $O_2$.

Still referring to FIG. 1, and in embodiments, hydrocarbon oil stream 2 may include whole crude oil, crude oil fractions, or combinations thereof. Whole crude oil may include crude oil as previously described. As described herein, "topped crude oil" is understood to mean a fraction of crude oil with boiling points less than 160° C. While the present description and examples may specify hydrocarbon oil 2 as the feedstock stream, it should be understood that the system 100, described with respect to the embodiments of FIG. 1, may be applicable for the conversion of a wide variety of crude oils, which may be present in the hydrocarbon oil stream 2. The hydrocarbon oil stream 2 may also include one or more non-hydrocarbon constituents, such as one or more heavy metals, sulfur compounds, nitrogen compounds, inorganic components, or other non-hydrocarbon compounds.

In embodiments, hydrocarbon oil stream 2 may be a heavy crude oil, which includes crude oil having an American Petroleum Institute (API) gravity of less than 35°, 34.5°, 34°, or 33°. In these embodiments, the crude oil may have a sulfur content of greater than or equal to 1.5 weight percent (wt. %), based on the total weight of the crude oil, such as greater than or equal to 1.6 wt. %, 1.7 wt. %, 1.75 wt. %, 1.8 wt. %, 1.9 wt. %, or 2.0 wt. %. By way of non-limiting example, the hydrocarbon oil stream 2 may be Arab Heavy crude oil, which has an API gravity of approximately 28° and a sulfur content of approximately 2.8 wt. %. In embodiments, the hydrocarbon oil stream 2 may be a light crude oil, which includes crude oil having an American Petroleum Institute (API) gravity of greater than 35°, 36°, 37°, or 38°. In these embodiments, the light crude oil may also be categorized as a sour light crude oil, which includes crude oil having a sulfur content of less than 1.5 weight percent (wt. %), based on the total weight of the crude oil, such as less than or equal to 1.4 wt. %, 1.3 wt. %, 1.2 wt. %, 1.1 wt. %, or 1.0 wt. %. By way of non-limiting example, the hydrocarbon oil stream 2 may be Arab Light crude oil, which has an API gravity of approximately 330 and a sulfur content of approximately 1.77 wt. %. By way of another non-limiting example, the hydrocarbon oil stream 2 may be Arab Extra Light crude oil, which has an API gravity of approximately 390 and a sulfur content of approximately 1.1 wt. %. In embodiments, the hydrocarbon oil stream 2 may be a combination of crude oils, such as, for example, a combination of Arab Light crude oil and Arab Extra Light crude oil. It should be understood that, as used herein, the "hydrocarbon oil stream" may refer to crude oil, which has not been previously treated, separated, or otherwise refined. Table 1 below set forth properties of an Arab light crude oil, as may be used in embodiments, herein.

TABLE 1

Arab Light Crude Oil Composition

| Property | Arab Light Crude |
| --- | --- |
| Density | 0.8537 |
| S (ppmw) | 1.94 |
| N (ppmw) | 830 |
| Ni (ppmw) | 3.1 |
| V (ppmw) | 10.2 |
| Na (ppmw) | 0.9 |
| Conradson Carbon (wt. %) | 4.25 |

In embodiments, the hydrocarbon oil stream 2 may have a density lower than 0.89 g/mL. In embodiments, the hydrocarbon oil stream 2 may have a density of from 0.75 g/mL to 0.92 g/mL, from 0.75 g/mL to 0.89 g/mL, from 0.75 g/mL to 0.87 g/mL, from 0.75 g/mL to 0.84 g/mL, from 0.84 g/mL to 0.92 g/mL, from 0.84 g/mL to 0.89 g/mL, from 0.84 g/mL to 0.87 g/mL, from 0.87 g/mL to 0.92 g/mL, from 0.87 g/mL to 0.89 g/mL, or from 0.89 g/mL to 0.92 g/Ml.

In embodiments, the hydrocarbon oil stream 2 may have from 44.92 wt. % to 66.0 wt. % of greater than 300° C. boiling point hydrocarbon fractions, as measured by the total weight of the hydrocarbon oil stream 2. The hydrocarbon oil stream may have from 30.65 wt. % to 55.08 wt. % of less than or equal to 300° C. boiling point hydrocarbon fractions, as measured by the total weight of the hydrocarbon oil stream 2. The hydrocarbon oil stream 2 may also have a remainder of non-hydrocarbon constituents.

In embodiments, the hydrocarbon oil stream 2 may have from 1 wt. % to 20 wt. %, from 1 wt. % to 16 wt. %, from 1 wt. % to 14 wt. %, from 1 wt. % to 10 wt. % from 1 wt. % to 8 wt. %, from 1 wt. % to 4 wt. %, from 4 wt. % to 20 wt. %, from 4 wt. % to 16 wt. %, from 4 wt. % to 14 wt. %, from 4 wt. % to 10 wt. %, from 4 wt. % to 8 wt. %, from 8 wt. % to 20 wt. %, from 8 wt. % to 16 wt. %, from 8 wt. % to 14 wt. %, from 8 wt. % to 10 wt. %, from 10 wt. % to 20 wt. %, from 10 wt. % to 16 wt. %, from 10 wt. % to 14 wt. %, from 14 wt. % to 20 wt. %, from 14 wt. % to 16 wt. %, or from 16 wt. % to 20 wt. % of >540° C. boiling point hydrocarbon fractions.

In embodiments, the heavy residual hydrocarbons 10 may include $C_{5+}$ hydrocarbons having boiling points of between 426° C. to 650° C. As mentioned earlier, the heavy residual hydrocarbons 10 may be a pitch product including, in part, asphaltenes. The heavy residual hydrocarbons 10 may also be atmospheric residue oil, vacuum residual oil, or both. In embodiments, the deasphalted oil stream 12 may include $C_1$ to $C_{5+}$ hydrocarbons having boiling points of between −162° C. to 650° C.

In embodiments, the syngas 16 may include primarily hydrogen and carbon monoxide. However, the syngas 16 may also include carbon dioxide. The gasification residue 14 may include residues such as char particles, ash, slag, and tar. The tar may in turn be used as a bunker fuel or furnace fuel. The ash or slag may also be petroleum coke. "Petroleum coke," as used herein may be needle coke, sponge coke, honeycomb coke, shot coke, or combinations thereof. The petroleum coke may be primarily composed of carbon, along with lesser amounts of non-hydrocarbon constituents. The petroleum coke may also be primarily composed of $C_{5+}$ hydrocarbons having boiling points of greater than 650° C.

As previously described, the gasification unit 106 may produce hydrogen as a product of the gasification reactions. In embodiments, the gasification unit 106 may produce hydrogen to carbon monoxide in a weight percent ratio of from 1:5 to 1:2 hydrogen to carbon monoxide. This may also include any weight percent ratio in between 1:5 to 1:2, such as, for example, 1:4, 1:3, 1:4.5, 1:3.5, or 1:2.5, as well as any combination of ratios therein. It is contemplated that the hydrogen generated by the gasification unit 106 may have the additional benefit of at least partially reducing the need for external sources of hydrogen for the hydrotreater 108 if the hydrogen from the gasification unit 106 is sent to the hydrotreater 108.

Still referring to FIG. 1, the hydrotreater 108 is fluidly connected to the solvent deasphalting unit 104 and hydrotreats at least the deasphalted oil stream 12 to form a light $C_{5+}$ hydrocarbon stream 26 and a heavy $C_{5+}$ hydrocarbon stream 28. In embodiments, the hydrotreater 108 may also hydrotreat at least the deasphalted oil stream 12 to additionally form a $C_1$ hydrocarbon stream 18 and a $C_2$-$C_4$ hydrocarbon stream 22. In embodiments, the $C_1$ hydrocarbon stream 18, the $C_2$-$C_4$ hydrocarbon stream 22, the light $C_{5+}$ hydrocarbon stream 26, and the heavy $C_{5+}$ hydrocarbon stream 28 may collectively be referred to herein as a hydrotreated product stream. In additional embodiments, the hydrotreater may additionally form a $C_{9+}$ heavy residual hydrocarbon stream, which may be recycled back to the gasification unit to produce additional syngas and gasification residue.

In embodiments, the hydrotreater 108 may be operated at a temperature of from 370° C. to 500° C. The hydrotreater 108 may be operated at a temperature of from 370° C. to 500° C., from 370° C. to 480° C., from 370° C. to 450° C., from 370° C. to 420° C., from 370° C. to 400° C., from 370° C. to 390° C., from 370° C. to 380° C., from 380° C. to 500° C., from 380° C. to 480° C., from 380° C. to 450° C., from 380° C. to 420° C., from 380° C. to 400° C., from 380° C. to 390° C., from 390° C. to 500° C., from 390° C. to 480° C., from 390° C. to 450° C., from 390° C. to 420° C., from 390° C. to 400° C., from 400° C. to 500° C., from 400° C. to 480° C., from 400° C. to 450° C., from 400° C. to 420° C., from 420° C. to 500° C., from 420° C. to 480° C., from 420° C. to 450° C., 450° C. to 500° C., from 450° C. to 480° C., or from 480° C. to 500° C. The hydrotreater 108 may be operated at a pressure of from 0.1 MPa to 0.2 MPa.

In embodiments, the hydrotreater 108 may have a liquid hourly space velocity of from 0.2 $h^{-1}$ to 0.7 $h^{-1}$. The hydrotreater 108 may have a liquid hourly space velocity of from 0.2 $h^{-1}$ to 0.7 $h^{-1}$, from 0.2 $h^{-1}$ to 0.6 $h^{-1}$, from 0.2 $h^{-1}$ to 0.5 $h^{-1}$, from 0.2 $h^{-1}$ to 0.4 $h^{-1}$, from 0.2 $h^{-1}$ to 0.3 $h^{-1}$, from 0.3 $h^{-1}$ to 0.7 $h^{-1}$, from 0.3 $h^{-1}$ to 0.6 $h^{-1}$, from 0.3 $h^{-1}$ to 0.5 $h^{-1}$, from 0.3 $h^{-1}$ to 0.4 $h^{-1}$, from 0.4 $h^{-1}$ to 0.7 $h^{-1}$, from 0.4 $h^{-1}$ to 0.6 $h^{-1}$, from 0.4 $h^{-1}$ to 0.5 $h^{-1}$, from 0.5 $h^{-1}$ to 0.7 $h^{-1}$, from 0.5 $h^{-1}$ to 0.6 $h^{-1}$, or from 0.6 $h^{-1}$ to 0.7 $h^{-1}$.

In embodiments, the hydrotreater 108 may include a hydrotreating catalyst. The hydrotreating catalyst may include an active-phase metal on a support. The active-phase metal may include nickel, molybdenum, tungsten, platinum, palladium, rhodium, ruthenium, gold, or combinations thereof. In embodiments, the support may include amorphous alumina, crystalline silica-alumina, alumina, silica, and combinations thereof. The hydrotreating catalyst may include MoNi on $Al_2O_3$, MoCo on $Al_2O_3$, $MoS_2$, maghemite, $Fe_3O_4$, nickel, NiO, $TiO_2$, $ZrO_2$, $CeO_2$, or combinations thereof.

In embodiments, the $C_2$-$C_4$ hydrocarbon stream 22 may generally include $C_2$-$C_4$ hydrocarbons, including $C_2$-$C_4$ paraffins, $C_2$-$C_4$ olefins, $C_2$-$C_4$ alkynes, or combinations thereof. The $C_2$-$C_4$ hydrocarbon stream 22 may include ethane, propane, butane, ethylene, propylene, butylene, ethyne, propyne, butyne, or combinations thereof. In embodiments, the light $C_{5+}$ hydrocarbon stream 26 may include $C_{5+}$ hydrocarbons having a having a $T_{95}$ boiling point (that is, the temperature at which greater than 95% of components are boiling in a hydrocarbon composition) of less than 200° C. The heavy $C_{5+}$ hydrocarbon stream 28 may include $C_{5+}$ hydrocarbons having a $T_5$ boiling point (that is, the temperature at which less than 5% of components are boiling in a hydrocarbon composition) of greater than or equal to 200° C. Accordingly, the temperature cut between the light $C_{5+}$ hydrocarbon stream 26 and the heavy $C_{5+}$ hydrocarbon stream 28 may be 200° C. However, the temperature cut between the light and heavy $C_{5+}$ hydrocarbon streams may also be greater or less than 200° C. depending upon the components in the hydrocarbon oil stream 2.

In embodiments, the heavy $C_{5+}$ hydrocarbon stream 28 may generally include residue having an API gravity of at least 8.0° and/or a standard liquid density of at least 1,000 kilograms per cubic meter ($kg/m^3$).

As previously mentioned, the steam enhanced catalytic crackers 114 include the first steam enhanced catalytic cracker and the second steam enhanced catalytic cracker. The first steam-enhanced catalytic cracker is fluidly connected to the hydrotreater 108 and cracks at least a portion of the light $C_{5+}$ hydrocarbon stream 26 to form a light steam enhanced catalytically cracked product 30. The second steam-enhanced catalytic cracker is fluidly connected to the hydrotreater 108 and cracks at least a portion of the heavy $C_{5+}$ hydrocarbon stream 28 to form a heavy steam enhanced catalytically cracked product 32. The first and second steam enhanced catalytic crackers are in parallel to each other and downstream of the hydrotreater 108. In embodiments, the steam enhanced catalytic crackers may also be fluidly connected to the deasphalting unit 104. In this configuration, the deasphalting unit 104 may send at least a portion of the deasphalted oil stream 10 to the steam enhanced catalytic crackers 114. In embodiments, the light steam enhanced catalytically cracked product 30, the heavy steam enhanced catalytically cracked product 32, or both may include olefins, aromatics, naphtha, or combinations thereof. The olefins may include ethylene, propylene, butylene, or combinations thereof. In embodiments, the olefins may additionally include gasoline.

In embodiments, the light and heavy $C_{5+}$ hydrocarbon streams may need to be processed at different conditions in the steam enhanced catalytic crackers 114 to maximize the yield of desired products. In one non-limiting example, the light $C_{5+}$ hydrocarbon stream 26 may require a longer residence time than the heavy $C_{5+}$ hydrocarbon stream 28 to fully treat and convert the light components of the light $C_{5+}$ hydrocarbon stream 26. Additionally, the heavy $C_{5+}$ hydrocarbon stream 28 may require a shorter residence time to avoid excessive coking of the components of the heavy $C_{5+}$ hydrocarbon stream 28. However, if two steam enhanced catalytic crackers are not available, the light $C_{5+}$ hydrocarbon stream 26 and the heavy $C_{5+}$ hydrocarbon stream 28 may be processed in one steam enhanced catalytic cracker at different conditions.

The first and second steam enhanced catalytic crackers may also generate different distributions of hydrocarbon products with their product streams. For example, and as illustrated in the Examples herein, the first steam enhanced catalytic cracker may generate a greater proportion of olefins than naphtha range products (including naphtha and gasoline). In embodiments, the first steam enhanced catalytic cracker may generate an olefin to naphtha product ratio of approximately 5:3 or approximately 11:6. The first steam enhanced catalytic cracker may also generate an olefin to naphtha product ratio of from 2:1, from 3:1, from 4:1, from 5:1, from 6:1, or from 7:1 olefins to naphtha.

Similarly, and as illustrated in the Examples herein, the second steam enhanced catalytic cracker may generate a greater proportion of naphtha and gasoline range products rather than olefins. In embodiments, the second steam enhanced catalytic cracker may generate an olefin to naphtha product ratio of approximately 4:3 or approximately 7:5 olefins to naphtha. The second steam enhanced catalytic cracker may also generate an olefin to naphtha product ratio of from 1.5:1, from 1.3:1, from 1.1:1, from 1:1, from 0.9:1, or from 0.8:1 olefins to naphtha.

The steam enhanced catalytic crackers 114 may be a riser type or a downer type cracker. As used herein, "riser type" reactors or units are those that have feed enter at the bottom of the reactor and exit at the type. As used herein, "downer type" reactors or units are those that have feed enter at the top of the reactor and exit at the bottom. For riser type crackers, it is contemplated that the residence time will generally be longer than for downer type crackers due to back-mixing of the feed stream as it rises in the riser type cracker. Conversely, for downer type crackers, it is contemplated that the residence time will generally be shorter than for the riser type crackers because of the effect of gravity on the feed stream. Therefore, in embodiments, the first steam enhanced catalytic cracker may be a riser type cracker and the second steam enhanced catalytic cracker may be a downer type cracker to take advantage of the relative residence times of the two. However, any combination of type-crackers may be used herein, such as riser-riser, downer-downer, downer-riser, etc.

In embodiments, the steam enhanced catalytic crackers 114 may operate with a residence time of between 0.5 seconds to 10 seconds. The steam enhanced catalytic crackers 114 may operate with a residence time of from 0.1 seconds to 20 seconds, from 0.1 to 15 seconds, from 0.1 to 10 seconds, from 0.1 to 5 seconds, from 0.1 to 1 seconds, from 0.1 to 0.5 seconds, from 0.5 to 20 seconds, from 0.5 to 15 seconds, from 0.5 to 10 seconds, from 0.5 to 5 seconds, from 0.5 to 1 seconds, from 1 to 20 seconds, from 1 to 15 seconds, from 1 to 10 seconds, from 1 to 5 seconds, from 5 to 20 seconds, from 5 to 15 seconds, from 5 to 10 seconds, from 10 to 20 seconds, from 10 to 15 seconds, or from 15 seconds to 20 seconds. As previously mentioned, the residence times may be different for the first and second steam enhanced catalytic crackers. In embodiments, the first steam enhanced catalytic cracker may have a residence time of from 3 seconds to 10 seconds, or any of the narrower ranges therein. The second steam enhanced catalytic cracker may have a residence time of from 1 second to 3 seconds, or any of the narrower ranges therein.

In embodiments, the steam enhanced catalytic crackers 114 may be fixed bed catalytic cracking reactors that may include steam and a cracking catalyst disposed within a steam cracking catalyst zone. The steam enhanced catalytic cracker may include a porous packing material, such as silica carbide packing, upstream of the steam cracking catalyst zone. The porous packing material may ensure sufficient heat transfer to the $C_{5+}$ hydrocarbon fraction and steam prior to conducting the steam enhanced catalytic cracking reaction in the steam cracking catalyst zone. Without being bound by theory, it is believed that a system that includes the steam enhanced catalytic cracking system 114 produces more light olefins compared to systems that incorporate conventional fluid catalytic cracking (FCC) units. Typically, FCC units are set up mainly to upgrade heavy feeds to gasoline and other transportation fuels. Further, typical FCC units are not set up to handle large quantities of steam like those used in steam enhanced catalytic cracking.

In embodiments, the cracking catalyst may be a nano-zeolite cracking catalyst including nano-zeolite particles. A variety of nano-zeolites may be suitable for the steam enhanced catalytic cracking reactions in the steam enhanced catalytic cracking reactors 114. The nano-zeolite cracking catalyst may include a structured zeolite, such as an MFI, a GIS, or a BEA structured zeolite, for example. In embodiments, the nano-zeolite cracking catalyst may include nano ZSM-5 zeolite, nano BEA zeolite, nano USY zeolite, combinations thereof. In embodiments, the nano-zeolite cracking catalyst may be loaded with phosphorous and a combination of heavy metals (e.g., metals having a density of greater than 5 g/cm$^3$), such as iron, lanthanum, cerium, zirconium, and combinations thereof. The nano-zeolites, such as nano-ZSM-5 zeolite, nano Beta zeolite, nano USY, or combinations thereof may be in hydrogen form. In hydrogen form, the Brønsted acid sites in the zeolite, also known as bridging OH—H groups, may form hydrogen bonds with other framework oxygen atoms in the zeolite framework.

In embodiments, the nano ZSM-5 zeolite, the nano Beta zeolite, the nano USY zeolite, or combinations thereof may have a molar ratio of silica to alumina to provide sufficient acidity to the nano-zeolite cracking catalyst to conduct the steam enhanced catalytic cracking reactions. The nano ZSM-5 zeolite, the nano Beta zeolite, the nano USY zeolite, or combinations thereof may have a molar ratio of silica to alumina of from 10 to 200, from 15 to 200, from 20 to 200, from 10 to 150, from 15 to 150, or from 20 to 150. The nano ZSM-5 zeolite, the nano Beta zeolite, the nano USY zeolite, or combinations thereof may have total acidity in the range of 0.2 millimoles/gram (mmol/g) to 2.5 mmol/g, 0.3 mmol/g to 2.5 mmol/g, 0.4 mmol/g to 2.5 mmol/g, 0.5 mmol/g to 2.5 mmol/g, 0.2 mmol/g to 2.0 mmol/g, 0.3 mmol/g to 2.0 mmol/g, 0.4 mmol/g to 2.0 mmol/g, or 0.5 mmol/g to 2.0 mmol/g. The nano ZSM-5 zeolite, the nano Beta zeolite, the nano USY zeolite, or combinations thereof may have an average crystal size of from 50 nanometer (nm) to 600 nm, from 60 nm to 600 nm, from 70 nm to 600 nm, from 80 nm to 600 nm, from 50 nm to 580 nm, or from 50 nm to 550 nm.

The nano-zeolite cracking catalyst may also include an alumina binder, which may be used to consolidate the nanoparticles of nano ZSM-5 zeolite, nano Beta zeolite, nano USY zeolite, or combinations thereof to form the nano-zeolite cracking catalyst. The nano-zeolite cracking catalyst may be prepared by combining the nano ZSM-5 zeolite, the nano Beta zeolite, the nano USY zeolite, or combinations thereof with the aluminum binder and extruding the nano-zeolite cracking catalyst to form pellets or other catalyst shapes. The nano-zeolite cracking catalyst may include from 10 weight percent (wt. %) to 80 wt. %, from 10 wt. % to 75 wt. %, from 10 wt. % to 70 wt. %, from 15 wt. % to 80 wt. %, from 15 wt. % to 75 wt. %, or from 15 wt. % to 70 wt. % alumina binder based on the total weight of the nano-zeolite cracking catalyst. The nano-zeolite cracking catalyst may have a mesoporous to microporous volume ratio in the range of from 0.5 to 1.5, from 0.6 to 1.5, from 0.7 to 1.5, from 0.5 to 1.0, from 0.6 to 1.0, or from 0.7 to 1.0.

In embodiments, the steam in the steam enhanced catalytic crackers 114 may reduce the hydrocarbon partial pressure, which may have the dual effects of increasing yields of light olefins and/or BTX as well as reducing coke formation. Light olefins like propylene and butylene are mainly generated from catalytic cracking reactions following the carbonium ion mechanism, and as these are intermediate products, they can undergo secondary reactions such as hydrogen transfer and aromatization (leading to coke formation). The steam may increase the yield of light olefins by suppressing these secondary bi-molecular reactions, and reduce the concentration of reactants and products, which favor selectivity towards light olefins. The steam may also suppress secondary reactions that are responsible for coke formation on catalyst surface, which is good for catalysts to maintain high average activation. These factors may show that a large steam-to-oil weight ratio may be beneficial to the production of light olefins.

In embodiments, and as previously mentioned, increasing the steam-to-feed ratio may improve the light olefin yield of the steam enhanced catalytic cracker. A ratio of the flowrate (gas hourly space velocity) of steam to the flowrate (gas hourly space velocity) of the feed (light $C_{5+}$ hydrocarbon stream 26 or heavy $C_{5+}$ hydrocarbon stream 28) to the steam enhanced catalytic cracking reactors 114 may be from 0.1 to 1.1 times, from 0.1 to 0.8 times, from 0.1 to 0.5 times, from 0.1 to 0.2 times, from 0.2 to 1.1 times, from 0.2 to 0.8 times, from 0.2 to 0.5 times, from 0.5 to 1.1 times, from 0.5 to 0.8 times, or from 0.8 to 1.1 times steam to feed to improve the steam enhanced catalytic cracking process. In embodiments, the ratio of steam to feed may be different for the first steam enhanced catalytic cracker and the second steam enhanced catalytic cracker. For example, the second steam enhanced catalytic cracker may have a steam to feed ratio of from 0.8 to 1.0 steam to feed, whereas the first steam enhanced catalytic cracker may have a steam to feed ratio of from 0.2 to 0.8. In embodiments, the higher steam to feed ratio may be beneficial for the heavy fractions due to the need to reduce the viscosity of heavier crude oil fraction as well as atomize the heavy fractions.

In embodiments, the steam may be injected into the steam enhanced catalytic crackers 114 at a gas hourly space velocity of greater than or equal to 0.1 h$^{-1}$, greater than or equal to 0.5 h$^{-1}$, greater than or equal to 1 h$^{-1}$, greater than or equal to 5 h$^{-1}$, greater than or equal to 6 h$^{-1}$, greater than or equal to 10 h$^{-1}$, or even greater than or equal to 15 h$^{-1}$. The steam may be introduced to the steam enhanced catalytic crackers 114 at a gas hourly space velocity of less than or equal to 100 h$^{-1}$, less than or equal to 75 h$^{-1}$, less than or equal to 50 h$^{-1}$, less than or equal to 30 h$^{-1}$, or less than or equal to 20 h$^{-1}$. The steam may be introduced to the steam enhanced catalytic crackers 114 at a gas hourly space velocity of from 0.1 h$^{-1}$ to 100 h$^{-1}$, from 0.1 h$^{-1}$ to 75 h$^{-1}$, from 0.1 h$^{-1}$ to 50 h$^{-1}$, from 0.1 h$^{-1}$ to 30 h$^{-1}$, from 0.1 h$^{-1}$ to 20 h$^{-1}$, from 1 h$^{-1}$ to 100 h$^{-1}$, from 1 h$^{-1}$ to 75 h$^{-1}$, from 1 h$^{-1}$ to 50 h$^{-1}$, from 1 h$^{-1}$ to 30 h$^{-1}$, from 1 h$^{-1}$ to 20 h$^{-1}$, from 5 h$^{-1}$ to 100 h$^{-1}$, from 5 h$^{-1}$ to 75 h$^{-1}$, from 5 h$^{-1}$ to 50 h$^{-1}$, from 5 h$^{-1}$ to 30 h$^{-1}$, from 5 h$^{-1}$ to 20 h$^{-1}$, from 6 h$^{-1}$ to 100 h$^{-1}$, from 6 h$^{-1}$ to 75 h$^{-1}$, from 6 h$^{-1}$ to 50 h$^{-1}$, from 6 h$^{-1}$ to 30 h$^{-1}$, from 6 h$^{-1}$ to 20 h$^{-1}$, from 10 h$^{-1}$ to 100 h$^{-1}$, from 10 h$^{-1}$ to 75 h$^{-1}$, from 10 h$^{-1}$ to 50 h$^{-1}$, from 10 h$^{-1}$ to 30 h$^{-1}$, from 10 h$^{-1}$ to 20 h$^{-1}$, from 15 h$^{-1}$ to 100 h$^{-1}$, from 15 h$^{-1}$ to 75 h$^{-1}$, from 15 h$^{-1}$ to 50 h$^{-1}$, from 15 h$^{-1}$ to 30 h$^{-1}$, or from 15 h$^{-1}$ to 20 h$^{-1}$.

In embodiments, the feed (light $C_{5+}$ hydrocarbon stream 26 or heavy $C_{5+}$ hydrocarbon stream 28) may be injected into the steam enhanced catalytic crackers 114 at a gas hourly space velocity of greater than or equal to 0.1 per hour (h$^{-1}$) or greater than or equal to 0.25 h$^{-1}$. The feed may be injected into the steam enhanced catalytic crackers 114 at a gas hourly space velocity of less than or equal to 50 h$^{-1}$, less than or equal to 25 h$^{-1}$, less than or equal to 20 h$^{-1}$, less than or equal to 14 h$^{-1}$, less than or equal to 9 h$^{-1}$, or less than or equal to 5 h$^{-1}$. The feed may be injected into the steam enhanced catalytic crackers 114 at a gas hourly space velocity of from 0.1 h$^{-1}$ to 50 h$^{-1}$, from 0.1 h$^{-1}$ to 25 h$^{-1}$, from 0.1 h$^{-1}$ to 20 h$^{-1}$, from 0.1 h$^{-1}$ to 14 h$^{-1}$, from 0.1 h$^{-1}$ to 9 h$^{-1}$, from 0.1 h$^{-1}$ to 5 h$^{-1}$, from 0.1 h$^{-1}$ to 4 h$^{-1}$, from 0.25 h$^{-1}$ to 50 h$^{-1}$, from 0.25 h$^{-1}$ to 25 h$^{-1}$, from 0.25 h$^{-1}$ to 20 h$^{-1}$, from 0.25 h$^{-1}$ to 14 h$^{-1}$, from 0.25 h$^{-1}$ to 9 h$^{-1}$, from 0.25 h$^{-1}$ to 5 h$^{-1}$, from 0.25 h$^{-1}$ to 4 v, from 1 h$^{-1}$ to 50 h$^{-1}$, from 1 h$^{-1}$ to 25 h$^{-1}$, from 1 h$^{-1}$ to 20 h$^{-1}$, from 1 h$^{-1}$ to 14 h$^{-1}$, from 1 h$^{-1}$ to 9 h$^{-1}$, or from 1 h$^{-1}$ to 5 h$^{-1}$.

In embodiments, the hourly space velocity may be different for the light steam enhanced catalytic cracker as compared to the heavy steam enhanced catalytic cracker. In one non-limiting example, the light $C_{5+}$ hydrocarbons stream 26 may require lesser hourly space velocities to give more time for the light $C_{5+}$ hydrocarbons stream 26 to be cracked into the desired products. In another non-limiting example, the heavy $C_{5+}$ hydrocarbons stream 28 may require greater hourly space velocities to prevent overcracking of the heavy $C_{5+}$ hydrocarbons stream 28 and prevent excess formation of petroleum coke. In embodiments, the hourly space velocity for the light steam enhanced catalytic cracker may be from 0.1 h$^{-1}$ to 1 h$^{-1}$. In embodiments, the hourly space velocity for the heavy steam enhanced catalytic cracker may be from 9 h$^{-1}$ to 40 h$^{-1}$.

In embodiments, the steam enhanced catalytic crackers 114 may operate at a temperature of from greater than or equal to 525° C., greater than or equal to 550° C., or greater than or equal to 575° C. The steam enhanced catalytic crackers 114 may be operated at a temperature of less than or equal to 750° C., less than or equal to 675° C., less than or equal to 650° C., or even less than or equal to 625° C. The steam enhanced catalytic crackers 114 may operate at temperatures of from 650° C. to 750° C. or from 675° C. to 750° C. The steam enhanced catalytic crackers 114 may be operated at temperatures of from 525° C. to 750° C., from 525° C. to 675° C., from 525° C. to 650° C., from 525° C. to 625° C., from 550° C. to 675° C., from 550° C. to 650° C., from 550° C. to 625° C., from 575° C. to 675° C., from 575° C. to 650° C., or from 575° C. to 625° C. The steam enhanced catalytic crackers 114 may be operated at a pressure of from 0.1 MPa to 0.2 MPa.

As previously discussed, the steam enhanced catalytic crackers 114 may produce olefins, and in particular, light olefins, such as ethylene, propylene, and butylene. In embodiments, the steam enhanced catalytic crackers may additionally produce gasoline as olefins. In embodiments, the ratio of olefins (gasoline) to light olefins produced may change depending on the operating temperatures used in the steam enhanced catalytic crackers 114. For example, operating temperatures between 500° C. to 650° C. may produce primarily propylene and gasoline over ethylene. As operating temperatures increase, the ratio moves further to producing primarily ethylene over propylene and gasoline. For example, operating temperatures between 650° C. to 680° C. may produce equal parts ethylene and propylene with less gasoline. At operating temperatures over 680° C., for example from 680° C. to 750° C., the reaction moves to primarily ethylene.

In embodiments, temperatures at the higher ends (>650° C.) of the operating range may be used to preferentially produce light olefins over heavier olefins, such as ethylene and propylene over gasoline. This may thereby make gasoline a by-product of the steam enhanced catalytic cracking reaction versus a primary product. Further temperature increases (>680° C.) may then minimize the amount of gasoline produced, primarily producing ethylene with propylene as a by-product. It is contemplated that the shifts discussed above may be related to reactions in the steam enhanced catalytic crackers moving from primarily catalytic cracking dominated at lower temperatures (500° C. to 650° C.) to primarily thermal cracking dominated at higher ends of the operating temperatures (>680° C.).

Still referring to FIG. 1, the integrated system 100 includes the product separator 116. The product separator 116 is fluidly connected to the first and second steam-enhanced catalytic crackers 114 and produces one or more product streams. The product streams may include an olefin product stream 42, a BTX product stream 44, and a naphtha product stream 46. Also as detailed further below, the one or more product streams may also include a reformate stream 48 and an aromatics complex stream 50. The olefin product stream 42 may include olefins, such as light olefins including ethylene, butylene, and propylene. The olefin product stream 42 may also include gasoline. The BTX product stream 44 may include aromatic compounds such as benzene, toluene, xylenes, or combinations thereof (also collectively referred to as "BTX"). The xylenes may include ortho-xylene, meta-xylene, and para-xylene. The naphtha product stream 46 may include naphtha, including light naphtha and heavy naphtha. The naphtha product stream 46 may also include cracked naphtha. In embodiments, the product streams may also include fuel oil (also known as heavy oil, marine fuel, or furnace oil), naphtha, off gas products ($C_1$-$C_4$ hydrocarbons), or combinations thereof. The fuel oil and off-gas products may alternatively be included as part of the one or more recycle streams. In embodiments, the product streams may include at least 50 wt. % $C_2$-$C_4$ light olefins. The product streams may also include at least 25 wt. % BTX. In embodiments, the one or more product streams may be combined into a single product stream.

In embodiments, the product separator 116 may also produce one or more recycle streams. The one or more recycle streams may include a methane cracker recycle stream 34, a steam cracker recycle stream 36, a hydrotreater recycle stream 38, or combinations thereof. The methane cracker recycle stream 34 may include $C_1$ hydrocarbons, which may be methane. The steam cracker recycle stream 36 may include $C_2$-$C_4$ hydrocarbons. The steam cracker recycle stream 36 may include $C_2$-$C_4$ paraffins, $C_2$-$C_4$ alkynes, or both. The steam cracker recycle stream 36 may include ethane, propane, butane, ethyne, propyne, butyne, or combinations thereof. The hydrotreater recycle stream 38 may include cracked naphtha, light cycle oil, heavy cycle oil, or combinations thereof. The hydrotreater recycle stream 38 may include all of the cracked naphtha that would otherwise be included in the naphtha product stream 46. The cracked naphtha may have boiling points of from an initial boiling point (IBP) of 25° C. to 204° C. The light cycle oil may have boiling points of between 343° C. to 426° C. The heavy cycle oil may have boiling points of greater than 426° C.

Still referring to FIG. 1, the system 100 includes the aromatics complex 118. The aromatics complex 118 is fluidly connected to the product separator 116 and processes the naphtha product stream 46 to produce benzene and xylenes. As illustrated in FIG. 1, the benzene and xylenes produced from the aromatics complex 118 may also be collectively referred to herein as an "aromatics complex product stream," 50. In embodiments, the aromatics complex 118 may further include a catalytic reformer 120 and a transalkylation unit 122.

In embodiments, the catalytic reformer 120 may be fluidly connected to product separator 116 and may catalytically reform the naphtha product stream 44 to produce a reformate stream 48. The reformate stream 48 may include benzene, toleuene, and xylenes. In embodiments, catalytically reforming the cracked naphtha that may be present in the naphtha product stream 44 may generate additional coke on catalysts in the catalytic reformer. The catalytic reformer may be operated at an operating temperature in the range of from 450° C. to 600° C., from 460° C. to 600° C., from 470° C. to 600° C., from 480° C. to 600° C., from 490° C. to 600° C., from 500° C. to 600° C., from 510° C. to 600° C., from 520° C. to 600° C., from 530° C. to 600° C., from 540° C. to 600° C., from 550° C. to 600° C., from 560° C. to 600° C., from 570° C. to 600° C., from 580° C. to 600° C., from 590° C. to 600° C., from 450° C. to 590° C., from 450° C. to 580° C., from 450° C. to 570° C., from 450° C. to 560° C., from 450° C. to 550° C., from 450° C. to 540° C., from 450° C. to 530° C., from 450° C. to 520° C., from 450° C. to 510° C., from 450° C. to 500° C., from 450° C. to 490° C., from 450° C. to 480° C., from 450° C. to 470° C., or from 450° C. to 460° C. In embodiments, the catalytic reformer 120 may be operated at an operating pressure in the range of from 0.7 MPa to 7 MPa.

In embodiments, the transalkylation unit 122 may be fluidly connected to the catalytic reformer 120 and may upgrade the toluene in the reformate stream 48 to produce additional benzene, xylenes, or both. The transalkylation unit 122 may also include a transalkylation catalyst. The transalkylation unit 122 may contact the reformate stream 48, particularly the toluene in the reformate stream 48, with hydrogen and the transalkylation catalyst to produce the benzene and xylenes. In embodiments, the transalkylation catalyst may have a mesostructure including at least one disordered mesophase and at least one ordered mesophase. As used in this disclosure, the term "ordered mesophase" may refer a crystalline zeolite having a uniform arrangement of mesopores, where "mesopores" have an average pore diameter between 2 nm and 50 nm. The term "disordered mesophase" may refer a non-uniform arrangement of mesopores, where mesopores have an average pore diameter between 2 nm and 50 nm. The term "ordered/disordered phase" may refer to the surface having a combination of at least one ordered mesophase and at least one disordered mesophase. Induction of an ordered/disordered phase into the zeolite structure increases the probability of larger molecules in a feed having access to the active sites inside the transalkylation catalyst 146.

In embodiments, the transalkylation catalyst may include a solid zeolite composite and a metal. The solid zeolite composite may include ZSM-5, ZSM$^{-11}$, ZSM$^{-12}$, ZSM-22, ZSM-23, Mordenite(MOR) framework zeolite, NES topology zeolite, EU$^{-1}$, MAPO-36, SAPO-5, SAPO$^{-11}$, SAPO-34, SAPO-41, or combinations thereof. The solid zeolite composite may include mesoporous Mordenite (MOR) zeolite and mesoporous ZSM-5 zeolite in a 1:1 to 5:1 weight ratio. The mesoporous Mordenite (MOR) zeolite may have a Si/Al molar ratio of at least 20, of from 20 to 300, of from 20 to 100, of from 25 to 50, or of from 28 to 32. In embodiments, the mesoporous ZSM-5 zeolite may have a Si/Al molar ratio of at least 5, such as from 5 to 500, from 10 to 100, from 20 to 75, from 30 to 50, from 35 to 45, or from 38 to 42. The transalkylation catalyst may further include the metal. The metal may include molybdenum, platinum, rhenium, nickel, or combinations thereof. In embodiments, the transalkylation unit 122 may be operated at an operating temperature in the range of from 350° C. to 500° C., from 400° C. to 500° C., from 350° C. to 450° C., or from 400° C. to 450° C., The transalkylation unit 122 may be operated at an operating pressure of from 1 MPa to 5 MPa.

In embodiments, the aromatics complex 118 may further include one or more extractive distillation units. The one or more extractive distillation units may include a solvent, such as, but not limited to, n-methyl-pyrrolidone or dimethylformamide. The one or more extractive distillation units may be in parallel with each other, in sequence, or combinations thereof. The one or more extractive distillation units may be fluidly connected to the catalytic reformer 120 and the transalkylation unit 122. The one or more extractive distillation units may separate the benzene, toluene, and xylenes in the reformate stream 48, as well as produce a $C_1$-$C_4$ hydrocarbon recycle stream 52 and a $C_{9+}$ hydrocarbon stream 54. The $C_1$-$C_4$ hydrocarbon recycle stream may generally include methane and $C_2$-$C_4$ hydrocarbons. The $C_{9+}$ hydrocarbon stream 54 may generally include hydrocarbons with greater than 9 carbon atoms.

In embodiments, the one or more extractive distillation units may also send the $C_1$-$C_4$ hydrocarbon recycle stream 52 to the product separator 116 to produce additional methane recycle stream 34, additional steam cracker recycle stream 36, or both. The one or more extractive distillation units may also send the $C_{9+}$ hydrocarbon stream 54 to the hydrotreater 108 to produce additional $C_1$ hydrocarbon stream 18, $C_2$-$C_4$ hydrocarbon stream 22, light $C_{5+}$ hydrocarbon stream 26, heavy $C_{5+}$ hydrocarbon stream 28, or combinations thereof.

In embodiments, the one or more extractive distillation units may also be downstream of the transalkylation unit 122. In these embodiments, the one or more extractive distillation units may separate the benzene and xylenes produced by the transalkylation unit 122. In these embodiments, the one or more extractive distillation units downstream of the transalkylation units may also produce the $C_1$-$C_4$ hydrocarbon recycle stream, the $C_{9+}$ hydrocarbon stream, or both.

In embodiments, the systems discussed herein may include additional components for the conversion of the hydrocarbon oil feedstocks. For example, the integrated system 100 may further include a methane cracker 110 fluidly connected to the hydrotreater 108 and product separator 116. The methane cracker 110 may crack the $C_1$ hydrocarbon stream 16, the methane cracker recycle stream 34, or both to produce hydrogen 16. The hydrogen 16 may be recycled and reused in the hydrotreater 108. In embodiments, the methane cracker may be operated at a temperature of from 850° C. to 1200° C. and at a pressure of from 0.1 MPa to 0.2 MPa. Without being bound by theory, hydrogen produced by methane cracking may also be incorporated in applications requiring pure hydrogen and no carbon monoxide (e.g., fuel cells).

As previously mentioned, and in embodiments, the hydrotreater 108 may include hydrogen 16. While the hydrogen 16 is discussed as coming from the methane cracker 110, it is also contemplated that the hydrogen 16 may come from additional sources, of which these additional sources may be the primary source for hydrogen used in the operation of the hydrotreater. In embodiments, the hydrotreater 108 may have a ratio of hydrogen 16 to feed (deasphalted oil stream 10) of from 800 L/L to 1200 L/L. The hydrotreater 108 may have a ratio of hydrogen 24 to feed of from 800 L/L to 1200 L/L, from 800 L/L to 1100 L/L, from 800 L/L to 1000 L/L, from 800 L/L to 900 L/L, from 900 L/L to 1200 L/L, from 900 L/L to 1100 L/L, from 900 L/L to 1000 L/L, from 1000

L/L to 1200 L/L, from 1000 L/L to 1100 L/L, from 1100 L/L to 1200 L/L, or from 1100 L/L to 1200 L/L.

In embodiments, the system 100 may further include a steam cracker 112. The steam cracker 112 may be fluidly connected to the hydrotreater 108 and product separator 116 and may crack the $C_2$-$C_4$ hydrocarbon stream 18, the steam cracker recycle stream 36, or both, to form a steam cracked product 20. The steam cracked product 20 may include a mixture of cracked hydrocarbon-based materials, which may be separated into one or more petrochemical products that are included in the first or second product streams. For example, the steam cracked product may include $C_2$-$C_4$ olefins, benzene, toluene, xylene, naphtha, or combinations thereof, and optionally, fuel gas, butadiene, $C_{5+}$ hydrocarbons, fuel oil, or combinations thereof. In embodiments, the steam cracker 112 may operate at a temperature of from 700° C. to 950° C., such as from 800° C. to 950° C. and at a pressure of from 0.1 MPa to 0.2 MPa. The steam cracker may operate with a residence time of from 0.05 seconds to 2 seconds. The mass ratio of steam to the $C_2$-$C_4$ hydrocarbon fraction 106 may be from about 0.3:1 to about 2:1.

In embodiments, the hydrotreater 108 may additionally be fluidly connected to the product separator 116 and may hydrotreat the hydrotreater recycle stream 38 to produce additional hydrotreater product stream. In embodiments, hydrotreating the cracked naphtha in the hydrotreater recycle stream 38 may saturate olefins and diolefins in the cracked naphtha, as well as removing impurities like sulfur and nitrogen, if still present. This may have the adding benefit of increasing the product streams' yield of olefins that would otherwise be converted to coke in the catalytic reformer 120 by direct processing of the cracked naphtha. In embodiments, the product separator 116 may send the methane recycle stream 30 to the methane cracker 110, the steam cracker recycle stream 36 to the steam cracker 112, the hydrotreater recycle stream 38 to the hydrotreater 108, or combinations thereof.

Figure 2:
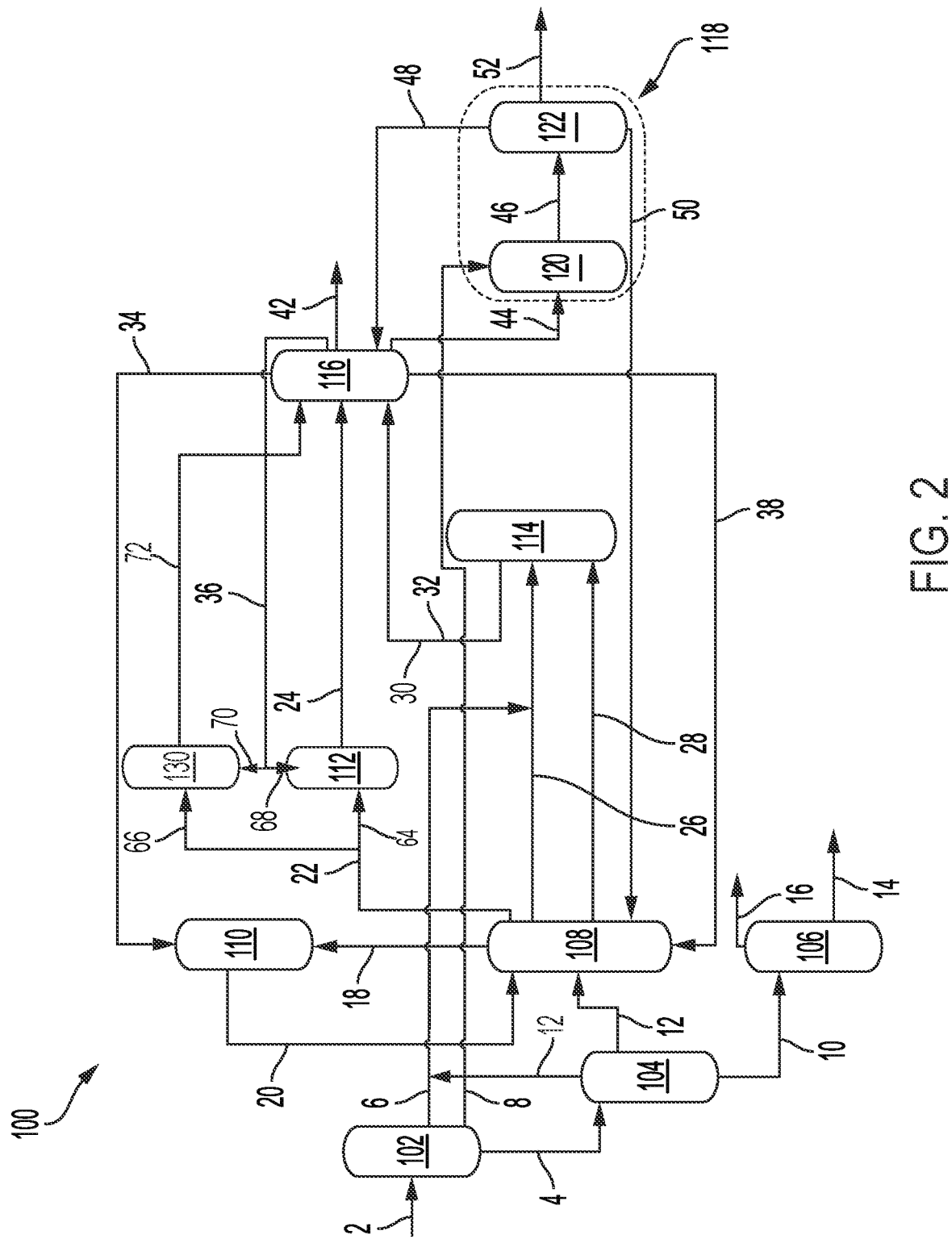
FIG. 2 illustrates a process flow diagram for an exemplary process in accordance with embodiments described herein.

Now referring to FIG. 2, and in embodiments, the integrated system 100 may also include a dehydrogenation unit 130. The dehydrogenation unit 130 may be fluidly connected to the hydrotreater 108 and the final product separator 116. The dehydrogenation unit 130 may dehydrogenate a $C_3$-$C_4$ portion 66 of the $C_2$-$C_4$ hydrocarbon stream 22, a $C_3$-$C_4$ portion (also referred to herein as a $C_3$-$C_4$ hydrocarbon recycle stream 70) of the steam cracker recycle stream 36, or both to form the propylene and butylene 72. In this configuration, the hydrotreater 108 may be additionally configured to produce a $C_3$-$C_4$ hydrocarbon stream 66, a $C_2$ hydrocarbon stream 64, or both. The dehydrogenation unit 130 may then send the propylene and butylene 72 to the final product separator 116, where the propylene and butylene 72 may be separated in the one or more product streams. In these embodiments, the steam cracker 112 may crack a $C_2$ portion 64 of the $C_2$-$C_4$ hydrocarbon stream 22, a $C_2$ portion (also referred to herein as a $C_2$ hydrocarbon recycle stream 68) of the steam cracker recycle stream 32, or both to form light olefins, naphtha, and BTX.

In embodiments, the dehydrogenation unit 130 may operate at a temperature of from 300° C. to 800° C., such as from 300° C. to 400° C., from 400° C. to 500° C., from 500° C. to 600° C., from 600° C. to 700° C., from 700° C. to 800° C., or any combinations thereof. The dehydrogenation unit 130 may also operate at a pressure of from 0.001 MPa to 1 MPa. Without being bound by any particular theory, it is believed that since the dehydrogenation of hydrocarbons is an endothermic reaction and conversion levels are limited by chemical equilibrium, it may be desirable to operate at relatively high temperatures and relatively low hydrogen partial pressures in order to achieve greater conversion. However, for reactions under severe conditions it may be difficult to maintain high activity and selectivity for long periods of time because undesirable side reactions such as aromatization, cracking, isomerization, coke formation, or combinations thereof, may increase. Therefore, reaction conditions may be selected with regard to maximizing one or more of catalytic activity, catalytic selectivity, and catalyst stability.

In embodiments, the dehydrogenation unit 130 may also include a catalyst system for conversion of hydrocarbons. The catalyst system may include a zincosilicate support material, one or more alkali or alkaline earth metals, and one or more platinum group metals. The zincosilicate support material may further include a MFI framework type structure incorporating at least silicon and zinc. As used herein, a "MFI framework type structure" may sometimes be referred to as a ZSM-5 framework type structure. Zeolitic framework types, such as the MFI framework type, are disclosed in "Atlas of Zeolite Framework Types, Fifth Edition" by Baerlcher, Meier, and Olson, the contents of which are incorporated by reference in their entirety. Dehydrogenating $C_3$-$C_4$ hydrocarbons may further include contacting the $C_3$-$C_4$ hydrocarbons with the catalyst system to dehydrogenate at least a portion of the $C_3$-$C_4$ hydrocarbons into the propylene and butylene.

In embodiments, the system 100 may further include a feed separator 102. The feed separator 102 may be a series of vapor-liquid separators such as flash tanks or flash drums (also referred to as a breakpot, knock-out drum, knock-out pot, compressor suction drum, or compressor inlet drum). It should be understood that a wide variety of fractionating separators may be utilized, such as distillation columns and the like.

The feed separator 102 may be fluidly connected to the solvent deasphalting unit 104, the light steam enhanced catalytic cracker 114, and the aromatics complex 118. The feed separator may initially separate the hydrocarbon oil stream 2 into a heavy oil fraction stream 4 and a light oil fraction stream. The feed separator 102 may then further separate the light oil fraction stream into at least a feed middle distillate stream 6 and a feed naphtha stream 8. The heavy oil fraction 4 may include hydrocarbons with boiling points of greater than 300° C. The light oil fraction may include hydrocarbons with boiling points of less than 300° C. The feed middle distillate stream 6 may include hydrocarbons, particularly distillates, with boiling points of between 204° C. and 300° C. The feed naphtha stream 8 may include hydrocarbons, particularly naphtha, with boiling points of between 185° C. and 204° C. In embodiments, the hydrocarbon oil stream 2 may include from 40 wt. % to 70 wt. % heavy hydrocarbon oil fraction 4. The hydrocarbon oil stream 2 may include from 36 wt. % to 72 wt. % light oil fraction. The hydrocarbon oil stream 2 may include from 30 wt. % to 60 wt. % middle distillate stream. The hydrocarbon oil stream 2 may include from 6 wt. % to 12 wt. % naphtha feed stream 8.

The feed separator 102 may send the feed middle distillate stream 6 to the steam enhanced catalytic crackers 114, the heavy oil fraction stream 4 to the solvent deasphalting unit 104, the feed naphtha stream 8 to the aromatics complex 118, or combinations thereof. The solvent deasphalting unit 104 may separate the heavy oil fraction stream 4 into at least the heavy residual hydrocarbons 10 and the de-asphalted oil stream 10. The first steam-enhanced catalytic cracker may crack the light oil fraction stream 6 into the light steam-enhanced catalytically cracked product 26. The aromatics complex 118 may process the naphtha feed stream 8 to produce additional benzene and xylenes.

In embodiments, the system may further include a hydrocracker. The hydrocracker may be used in place of the hydrotreater 108 to upgrade the deasphalted oil stream 12 to produce hydrocracker product streams in place of the hydrotreater product streams. In embodiments with the hydrocracker in place of the hydrotreater 108, the hydrocracker may provide the additional advantage of cracking the heaviest hydrocarbon components of the deasphalted oil stream 12 to form olefins, BTX, and naphtha, similar to the function of the second steam enhanced catalytic cracker.

In other embodiments, the hydrocracker may be included in addition to the hydrotreater 108. In these embodiments, the hydrocracker may be downstream of and fluidly connected to the hydrotreater 108. The hydrocracker may also be fluidly connected to the product separator 116. The hydrotreater 108 may be additionally configured to send at least a portion of the heavy $C_{5+}$ hydrocarbon stream 28 to the hydrocracker as a heaviest $C_{5+}$ hydrocarbon stream. The heaviest $C_{5+}$ hydrocarbon stream may include $C_{5+}$ hydrocarbons having boiling points of from 540° C. to 640° C. In embodiments, the heaviest $C_{5+}$ hydrocarbon stream may also generally include the hydrocarbon residues having an API gravity of at least 8.0° and/or a standard liquid density of at least 1,000 kilograms per cubic meter (kg/m$^3$), as previously mentioned. The hydrocracker may crack the heaviest $C_{5+}$ hydrocarbon stream to form olefins, BTX, and naphtha. The hydrocracker may also be additionally configured to send the olefins, BTX, and naphtha to the product separator 116.

Still referring to FIGS. 1, embodiments of the present disclosure also include integrated processes for upgrading a hydrocarbon oil feed stream. The processes may include any of the integrated systems 100 previously described. The process includes solvent deasphalting the hydrocarbon oil stream 2 to form at least the deasphalted oil stream 12 and the heavy residual hydrocarbons 10. The process further includes processing the heavy residual hydrocarbons 10 to form the gasification residue 14 and the syngas 16. The process further includes hydrotreating at least the deasphalted oil stream 12 to form the light $C_{5+}$ hydrocarbon stream 26 and the heavy $C_{5+}$ hydrocarbon stream 28. The process further includes steam enhanced catalytically cracking the light $C_{5+}$ hydrocarbon stream 26 to form the light steam enhanced catalytically cracked product 30. The process further includes steam enhanced catalytically cracking the heavy $C_{5+}$ hydrocarbon stream 28 to form the heavy steam enhanced catalytically cracked product 32. The process further includes passing at least a portion of the light steam enhanced catalytically cracked stream 26, the heavy steam enhanced catalytic cracker product stream 32, or both to the product separator 116 to produce the olefin product stream 42, the naphtha product stream 46, and the BTX product stream 44. The process further includes processing the naphtha product stream 46 in the aromatics complex 118 to produce benzene and xylenes as part of the aromatics complex product stream 50.

In embodiments, processing the naphtha product stream 46 in the aromatics complex 118 may further include catalytically reforming the naphtha product stream 46 to produce the reformate stream 48 and upgrading the toluene in the reformate stream 48 in the transalkylation unit 122 to form additional benzene, xylenes, or both. Processing the naphtha product stream 46 in the aromatics complex 118 may also include passing at least a portion of the reformate stream 48 through one or more extractive distillation units to separate the benzene, toluene, and xylenes, produce the $C_1$-$C_4$ hydrocarbon recycle stream 52, and produce the $C_{9+}$ hydrocarbon stream 54. In embodiments, the previous step may occur before upgrading the toluene in the reformate stream 48 in the transalkylation unit 122.

In embodiments, the process may further include hydrotreating the hydrotreater recycle stream 38 to form additional hydrotreated product stream, methane cracking the $C_1$ hydrocarbon stream 16, the methane recycle stream 30, or both to form hydrogen 16, steam cracking the $C_2$-$C_4$ hydrocarbon stream 18, the steam cracker recycle stream 36, or both to form the steam cracked product 20. The process may also further include passing the hydrogen 16 to the hydrotreater 108 to be recycled in the hydrotreater 108 and passing the steam cracked product 20 to the final separator 116 to produce the one or more product streams and the one or more recycle streams.

In embodiments, the process may also further include passing the $C_1$-$C_4$ hydrocarbon recycle stream 52 to the product separator to produce additional methane recycle stream 34, additional steam cracker recycle stream 36, or both. The process may also include passing the $C_{9+}$ hydrocarbon stream 54 to the hydrotreater to produce additional $C_1$ hydrocarbon stream 18, $C_2$-$C_4$ hydrocarbon stream 22, light $C_{5+}$ hydrocarbon stream 26, heavy $C_{5+}$ hydrocarbon stream 28, or combinations thereof.

In embodiments including the dehydrogenation unit, the process may further include steam cracking a $C_2$ portion of the $C_2$-$C_4$ hydrocarbon stream 18, a $C_2$ portion of the steam cracker recycle stream 36, or both, to form light olefins, naphtha, and BTX. The process may also further include dehydrogenating a $C_3$-$C_4$ portion of the $C_2$-$C_4$ hydrocarbon stream 18, a $C_3$-$C_4$ portion of the steam cracker recycle stream 36, or both to form propylene and butylene. The process may also further yet include passing the propylene and butylene to the final separator 116 to produce the one or more product streams.

In embodiments including the first product separator 118, the process may further include passing the hydrotreated product stream to the first product separator 118 to separate the $C_1$ hydrocarbon stream 16, the $C_2$-$C_4$ hydrocarbon stream 18, the light $C_{5+}$ hydrocarbon stream 26, the heavy $C_{5+}$ hydrocarbon stream 28, or combinations thereof.

The process may also further include solvent deasphalting the heavy hydrocarbon fraction 4 to form at least the deasphalted oil stream 12 and the heavy residual hydrocarbons 10. The process may also further yet include steam enhanced catalytically cracking at least the light hydrocarbon fraction 6 in the first steam enhanced catalytic cracker to form the light steam enhanced catalytically cracked product 26. In embodiments including the feed separator 102, the process may further include initially passing the hydrocarbon oil stream 2 through the feed separator 102 to separate the hydrocarbon oil stream 2 into the heavy hydrocarbon fraction 4, the light hydrocarbon fraction 6, and the feed naphtha stream 8. The process may also further yet include solvent deasphalting the heavy hydrocarbon fraction 4 to form at least the deasphalted oil stream 12 and the heavy residual hydrocarbons 10. The process may also further yet include steam enhanced catalytically cracking at least the light hydrocarbon fraction 6 in the first steam enhanced catalytic cracker to form the light steam enhanced catalytically cracked product 30. The process may also further yet include processing the feed naphtha stream 8 in the aromatics complex 118 to produce additional benzene and xylenes.

EXAMPLES

The various embodiments of methods and systems for the conversion of a hydrocarbon oil will be further clarified by the following examples. The examples are illustrative in nature, and should not be understood to limit the subject matter of the present disclosure.

Example 1

Arab light crude oil (AL), Arab extra light crude oil (AXL), and Arab heavy crude oil (AH) were processed in a simulation program using the systems illustrated in FIGS. 1 and 2. The composition of the crude oils used in the Examples are shown below in Tables 2 and 3.

TABLE 2

Arab Extra Light, Arab Light, and Arab Heavy Crude Oil Compositions

| Feed | AXL | AL | AH |
|---|---|---|---|
| Density at 15.6° C. | 0.8412 | 0.8658 | 0.8871 |
| Percentage $C_1$-$C_4$ hydrocarbon fractions | 5.49 | 4.46 | 3.25 |
| Percentage <300° C. boiling point hydrocarbon fractions | 49.59 | 39.85 | 30.65 |
| Percentage >300° C. boiling point hydrocarbon fractions | 44.92 | 55.69 | 66.0 |

TABLE 3

Arab Extra Light, Arab Light, and Arab Heavy Crude Oil Compositions

| Feed | AXL | AL | AH |
|---|---|---|---|
| Light Fraction (< 300° C. boiling point) | | | |
| Percentage C1-C5 hydrocarbons | 5.49 | 4.46 | 3.25 |
| Liquefied Natural Gas (C5 hydrocarbons to <300° C. boiling point fractions) | 49.59 | 39.85 | 30.65 |
| Heavy Fraction (>300° C. boiling point) | | | |
| 300° C. to 385° C. boiling point hydrocarbon fractions (diesel products) | 15.01 | 13.96 | 13.24 |
| 385° C. to 540° C. boiling point hydrocarbon fractions (vacuum gas oil) | 18.59 | 20.18 | 19.3 |
| >540° C. boiling point hydrocarbon fractions (vacuum residuals) | 11.32 | 21.55 | 33.56 |

Table 4 below illustrates the simulation results using Arab extra light crude oil as the feedstock hydrocarbon oil. The simulation was performed according to the configuration illustrated in FIG. 1 for Inventive Example 1 and FIG. 2 for Inventive Example 2. Similarly, Comparative Example 1 were performed according to FIG. 1, but without the solvent deasphalting unit or the gasification unit. Comparative Example 2 was performed according to FIG. 2, but without the dehydrogenation unit. Comparative Example 3 was also performed according to FIG. 2, but without the gasification unit or deasphalting unit.

TABLE 4

Inventive Example Testing Overall Yield

| | Example # | | | | |
|---|---|---|---|---|---|
| Component | Inventive Example 1 | Inventive Example 2 | Comparative Example 1 | Comparative Example 2 | Comparative Example 3 |
| | Weight Percentage Component | | | | |
| Hydrogen | 3.1 | 2.6 | 3.3 | 2.6 | 2.7 |
| Petroleum Coke | 4.3 | 3.1 | 4.6 | 3.1 | 3.3 |
| Ethylene | 12.6 | 10.4 | 13.6 | 10.4 | 11.1 |
| Propylene | 23.1 | 25.0 | 24.7 | 21.9 | 26.7 |
| Butylene | 13.1 | 15.8 | 13.9 | 12.9 | 16.7 |
| BTX | 26.8 | 27.1 | 26.8 | 27.1 | 28.2 |
| Purge and Other Components | 17.1 | 16.0 | 13 | 21.9 | 11.3 |

In Table 4, above, the "Purge and Other Products" may include crude oil fractions not previously mentioned in the preceding components. The Purge and Other Products may also include waste or unusable streams. For example, the Purge and Other Products may include light cycle oils, heavy cycle oils, distillate, and $C_1$, and $C_2$-$C_4$ paraffins. The heavy cycle oil may be used, for example, as fuel oil for boilers.

In Table 4 above, it is contemplated that the greater amount of olefins present in Comparative Example 1 as compared to Inventive Example 1 is due to the exclusion of the deasphalting unit and gasification unit. Because the deasphalting unit and gasification unit are excluded in comparative example 1, the heavy streams ordinarily processed in the gasification unit and deasphalting unit are instead sent to the steam enhanced catalytic crackers. This increases the throughput in the steam enhanced catalytic crackers and thus the olefin yield. However, this configuration also results in a lesser amount of naphtha and syngas within the product streams, which may in turn reduce the yields of BTX if the naphtha is later processed and upgraded to aromatics such as benzene, toluene, and xylenes. However, this phenomenon may also be dependent on the crude oil feed that is chosen. For example, it is contemplated that processing Arab heavy crude oil, with its greater amounts of heavier (greater boiling point) hydrocarbon components, would show a marked reduction in generation of both olefins and naphtha when the solvent deasphalting unit and gasification unit were not included. This may illustrate the particular suitability of the systems discussed herein towards processing and upgrading of heavier grades of crude oil.

Tables 5 and 6 below illustrate the simulation results for Inventive Example 1. The simulation was performed according to the configuration illustrated in FIG. 1, but without recycle streams from the product separator.

TABLE 5

Inventive Example 1 Product Yields by Processing Unit

| Gasification Unit | | Hydrotreater | | Steam Cracker | |
|---|---|---|---|---|---|
| Product | wt. % | Product | wt. % | Product | wt. % |
| Syngas | 30.0 | Methane and Hydrogen | 1.6 | Methane and Hydrogen | 22.7 |
| Gasification Residue | 70.0 | Liquefied Petroleum Gas ($C_2$ to $C_4$) | 0.3 | Ethylene | 46.7 |
| | | | | Propylene | 13.8 |
| | | | | Butadiene | 2.9 |
| | | Naphtha | 29 | BTX | 0 |

TABLE 5-continued

Inventive Example 1 Product Yields by Processing Unit

| Gasification Unit | | Hydrotreater | | Steam Cracker | |
|---|---|---|---|---|---|
| Product | wt. % | Product | wt. % | Product | wt. % |
| | | (185° C. to 204° C.) | | C5+ Hydrocarbons | 10.1 |
| | | Distillate (204° C. to 343° C.) | 52.7 | Fuel Oil | 2.4 |
| | | Gas Oil | 16.1 | | |
| | | Heavy Cycle Oil & Atmospheric Residue Oil (>340° C.) | 0 | | |

TABLE 6

Inventive Example 1 Product Yields by Processing Unit Continued

| SECC for Light Fraction | | SECC for Heavy Fraction | | Catalytic Reformer | | Transalkylation Unit | |
|---|---|---|---|---|---|---|---|
| Product | wt. % | Product | wt. % | Product | wt. % | Product | wt. % |
| Methane | 4.6 | Methane | 3.4 | C1 + H2 | 2.1 | C1 + H2 | 0.5 |
| Non-Olefin C2-C4 Hydrocarbons | 2.7 | Non-Olefin C2-C4 Hydrocarbons | 8.5 | Non-Olefin C2-C4 Hydrocarbons | 6.1 | Non-Olefin C2-C4 Hydrocarbons | 3.7 |
| C2-C4 Olefins | 44.2 | C2-C4 Olefins | 37.9 | Naphtha | 24.4 | Naphtha | 0.5 |
| Naphtha & Gasoline | 26.9 | Naphtha & Gasoline | 28 | Benzene | 4.9 | Benzene | 5.1 |
| Light Cycle Oil | 17.4 | Light Cycle Oil | 7.8 | Toluene | 16.4 | Toluene | 0.5 |
| Heavy Cycle Oil | 1.2 | Heavy Cycle Oil | 7.3 | Xylenes | 23.6 | Xylenes | 72.6 |
| Coke | 3 | Coke | 7 | C9+ | 22.4 | C9+ | 17.1 |

Referring to Tables 5 and 6 above, the Arab extra light crude oil illustrated in Table 3 was first sent to a deasphalting unit, wherein the heavy residual hydrocarbons were sent to the gasification unit and all other components were sent to the hydrotreater. In regards to the hydrotreater, the methane and hydrogen were sent to a methane cracker for production of primarily hydrogen. The liquefied petroleum gas was sent to the steam cracker, for conversion to the steam cracker products. The naphtha from the hydrotreater was sent to the first steam enhanced catalytic cracker, for conversion to the first steam enhanced catalytic cracker products. The distillate, gas oil, heavy cycle oil, and atmospheric residue oil were sent to the second steam enhanced catalytic cracker, for conversion to the second steam enhanced catalytic cracker products. The distillate was primarily composed of diesel and kerosene boiling point hydrocarbon fractions.

All of the steam cracker products were sent to the product separator. All of the products from both of the steam enhanced catalytic crackers were also sent to the product separator. The naphtha and gasoline stream was then sent to the catalytic reformer, which sent its products to the transalkylation unit.

Tables 7 and 8 below illustrate the simulation results for Comparative Example 1. The simulation was performed similar to Inventive Example 1, but without the deasphalting unit or gasification unit.

TABLE 7

Comparative Example 1 Product Yields by Processing Unit

| Gasification Unit | | Hydrotreater | | Steam Cracker | |
|---|---|---|---|---|---|
| Product | wt. % | Product | wt. % | Product | wt. % |
| Syngas | 30.0 | Methane and Hydrogen | 1.6 | Methane and Hydrogen | 22.6 |
| Gasification Residue | 70.0 | Liquefied Petroleum Gas (C2 to C4) | 0.3 | Ethylene | 47.2 |
| | | | | Propylene | 13.7 |
| | | | | Butadiene | 2.9 |

TABLE 7-continued

Comparative Example 1 Product Yields by Processing Unit

| Gasification Unit | | Hydrotreater | | Steam Cracker | |
|---|---|---|---|---|---|
| Product | wt. % | Product | wt. % | Product | wt. % |
| | | Naphtha (185° C. to 204° C.) | 23.9 | BTX | 0 |
| | | Distillate (204° C. to 343° C.) | 53.4 | C5+ Hydrocarbons | 10 |
| | | | | Fuel Oil | 2.4 |
| | | Gas Oil | 20.4 | | |
| | | Heavy Cycle Oil & Atmospheric Residue Oil (>340° C.) | 0.3 | | |

TABLE 8

Comparative Example 1 Product Yields by Processing Unit Continued

| SECC for Light Fraction | | SECC for Heavy Fraction | | Catalytic Reformer | | Transalkylation Unit | |
|---|---|---|---|---|---|---|---|
| Product | wt. % | Product | wt. % | Product | wt. % | Product | wt. % |
| Methane | 4.9 | Methane | 3.5 | C1 + H2 | 2.2 | C1 + H2 | 0.5 |
| Non-Olefin C2-C4 Hydrocarbons | 2.8 | Non-Olefin C2-C4 Hydrocarbons | 8.2 | Non-Olefin C2-C4 Hydrocarbons | 6.2 | Non-Olefin C2-C4 Hydrocarbons | 3.7 |
| C2-C4 Olefins | 46.1 | C2-C4 Olefins | 37 | Naphtha | 23.1 | Naphtha | 0.5 |
| Naphtha & Gasoline | 25 | Naphtha & Gasoline | 26.2 | Benzene | 5 | Benzene | 5.1 |
| Light Cycle Oil | 17.1 | Light Cycle Oil | 9.4 | Toluene | 16.7 | Toluene | 0.5 |
| Heavy Cycle Oil | 1 | Heavy Cycle Oil | 9.4 | Xylenes | 24 | Xylenes | 72.6 |
| Coke | 3 | Coke | 6.4 | C9+ | 22.8 | C9+ | 17.1 | le;.4qAs illustrated in Tables 4-8 above, separating the heavy residual hydrocarbons before processing the Arab Extra Light Crude Oil in the hydrotreater resulted in a higher concentration of products in the naphtha boiling point range for the hydrotreater of approximately 5.1 wt. %.

Tables 9 and 10 below illustrate the simulation results for Inventive Example 2. The simulation was performed according to the configuration illustrated in FIG. 2, i.e. FIG. 1 but with the dehydrogenation unit and without the recycle streams. Although not listed in Tables 9 and 10 below, $C_3$ and $C_4$ hydrocarbons entering the dehydrogenation unit had approximately a 100%~conversion rate to propylene and butylene, respectively.

TABLE 9

Inventive Example 2 Product Yields by Processing Unit

| Gasification Unit | | Hydrotreater | | Steam Cracker | |
|---|---|---|---|---|---|
| Product | wt. % | Product | wt. % | Product | wt. % |
| Syngas Gasification | 30.0 70.0 | Methane and Hydrogen | 1.6 | Methane and Hydrogen | 18.3 |
| | | Residue | | Ethylene | 59 |
| | | Liquefied Petroleum Gas ($C_2$ to $C_4$) | 0.3 | Propylene | 9.1 |
| | | | | Butadiene | 2.7 |
| | | Naphtha (185° C. to 204° C.) | 29 | BTX | 0 |
| | | | | C5+ Hydrocarbons | 7.8 |
| | | Distillate (204° C. to 343° C.) | 52.7 | Fuel Oil | 2 |
| | | Gas Oil | 16.1 | | |
| | | Heavy Cycle Oil & Atmospheric Residue Oil (>340° C.) | 0 | | |

TABLE 10

Inventive Example 2 Product Yields by Processing Unit Continued

| SECC for Light Fraction | | SECC for Heavy Fraction | | Catalytic Reformer | | Transalkylation Unit | |
|---|---|---|---|---|---|---|---|
| Product | wt. % | Product | wt. % | Product | wt. % | Product | wt. % |
| Methane | 4.6 | Methane | 3.4 | C1 + H2 | 2.1 | C1 + H2 | 0.5 |
| Non-Olefin C2-C4 Hydrocarbons | 2.7 | Non-Olefin C2-C4 Hydrocarbons | 8.5 | Non-Olefin C2-C4 Hydrocarbons | 6.1 | Non-Olefin C2-C4 Hydrocarbons | 3.7 |
| C2-C4 Olefins | 44.2 | C2-C4 Olefins | 37.9 | Naphtha | 24.4 | Naphtha | 0.5 |
| Naphtha & Gasoline | 26.9 | Naphtha & Gasoline | 28 | Benzene | 4.9 | Benzene | 5.1 |
| Light Cycle Oil | 17.4 | Light Cycle Oil | 7.8 | Toluene | 16.4 | Toluene | 0.5 |
| Heavy Cycle Oil | 1.2 | Heavy Cycle Oil | 7.3 | Xylenes | 23.6 | Xylenes | 72.6 |
| Coke | 3 | Coke | 7 | C9+ | 22.4 | C9+ | 17.1 |

As illustrated by Inventive Example 2 and Comparative Example 2 in Table 4 above, including the dehydrogenation unit resulted in a higher concentrations of olefins in the final product stream while not affecting the yield of the BTX. For example, inclusion of the dehydrogenation unit resulted in an increase in olefin yield in the final product stream of approximately 6.0 wt. %, comparing Inventive Example 2 and Comparative Example 2.

The present application discloses several technical aspects. One aspect is an integrated process for upgrading a hydrocarbon oil feed stream utilizing a gasification unit, steam enhanced catalytic cracker, and an aromatics complex the method including: solvent deasphalting the hydrocarbon oil stream to form at least a deasphalted oil stream and heavy residual hydrocarbons, the heavy residual hydrocarbons including at least asphaltenes; processing the heavy residual hydrocarbons in a gasification unit to form syngas and gasification residue; hydrotreating the deasphalted oil stream to form a light $C_{5+}$ hydrocarbon stream, and a heavy $C_{5+}$ hydrocarbon stream; steam enhanced catalytically cracking the light $C_{5+}$ hydrocarbon stream to form a light steam enhanced catalytically cracked product including olefins, BTX, naphtha, or combinations thereof; steam enhanced catalytically cracking the heavy $C_{5+}$ hydrocarbon stream to form a heavy steam enhanced catalytically cracked product including olefins, BTX, naphtha, or combinations thereof; passing at least a portion of the light steam enhanced catalytically cracked stream, the heavy steam enhanced catalytically cracked stream, or both to a product separator to produce a olefin product stream, a naphtha product stream, and a BTX product stream; and processing the naphtha product stream in the aromatics complex to produce benzene and xylenes, and wherein a ratio of gas hourly space velocity of steam to gas hourly space velocity of $C_{5+}$ hydrocarbon stream in the first and second steam enhanced catalytic crackers is from 0.1 to 1.1 times steam to $C_{5+}$ hydrocarbon stream.

A second aspect may include the first aspect, wherein processing the naphtha product stream in the aromatics complex further includes catalytically reforming the naphtha product stream to produce a reformate stream including benzene, toluene, and xylene; and upgrading the toluene in the reformate stream in a transalkylation unit to form additional benzene, xylenes, or both.

A third aspect may include any one of the first through second aspects, wherein the light $C_{5+}$ hydrocarbon fraction includes $C_{5+}$ hydrocarbons having a $T_{95}$ boiling point of less than 200° C.; and the heavy $C_{5+}$ hydrocarbon fraction includes $C_{5+}$ hydrocarbons having a $T_5$ boiling point of greater than or equal to 200° C.

A fourth aspect may include any one of the first through third aspects, wherein hydrotreating the deasphalted oil stream additionally forms a $C_1$ hydrocarbon stream and a $C_2$-$C_4$ hydrocarbon stream; and the $C_1$ hydrocarbon stream, the $C_2$-$C_4$ hydrocarbon stream, the light $C_{5+}$ hydrocarbon stream, and the heavy $C_{5+}$ hydrocarbon stream together include a hydrotreated product stream.

A fifth aspect may include the fourth aspect, further including methane cracking the $C_1$ hydrocarbon stream to form hydrogen; steam cracking the $C_2$-$C_4$ hydrocarbon stream to form a steam cracked product including light olefins, naphtha, and BTX; and passing the steam cracked product to the final separator to produce the one or more product streams and the one or more recycle streams.

A sixth aspect may include the fifth aspect, wherein the one or more recycle streams include a methane recycle stream, a steam cracker recycle stream, a hydrotreater recycle stream, or combinations thereof; the steam cracker recycle stream includes $C_2$-$C_4$ hydrocarbons; the hydrotreater recycle stream includes cracked naphtha, light cycle oil, and heavy cycle oil having boiling points of between 185° C. to 650° C.

A seventh aspect may include the sixth aspect, further including hydrotreating the hydrotreater recycle stream to form additional $C_1$ hydrocarbon stream, $C_2$-$C_4$ hydrocarbon stream, light $C_{5+}$ hydrocarbon stream, heavy $C_{5+}$ hydrocarbon stream, or combinations thereof; methane cracking the methane recycle stream to form additional hydrogen; steam cracking the steam cracker recycle stream to form additional steam cracked product; and passing the hydrogen to the hydrotreater to be recycled in the hydrotreater.

An eighth aspect may include the seventh aspect, further including processing the naphtha product stream in the aromatics complex, further including catalytically reforming the naphtha to produce a reformate stream including benzene, toluene, and xylene, passing at least a portion of the reformate stream through one or more extractive distillation units to separate the benzene, toluene, and xylenes, produce a $C_1$-$C_4$ hydrocarbon recycle stream, and produce a $C_{9+}$ hydrocarbon stream, and upgrading the toluene in a transalkylation unit to form additional benzene, xylenes, or both; passing the $C_1$-$C_4$ hydrocarbon recycle stream to the product separator to produce additional methane recycle stream, additional steam cracker recycle stream, or both; and passing the $C_{9+}$ hydrocarbon stream to the hydrotreater to produce additional $C_1$ hydrocarbon stream, $C_2$-$C_4$ hydrocarbon stream, light $C_{5+}$ hydrocarbon stream, heavy $C_{5+}$ hydrocarbon stream, or combinations thereof.

A ninth aspect may include any one the sixth through eighth aspects, further including steam cracking a $C_2$ portion of the $C_2$-$C_4$ hydrocarbon stream, a $C_2$ portion of the steam cracker recycle stream, or both, to form the steam cracked product; and dehydrogenating a $C_3$-$C_4$ portion of the $C_2$-$C_4$ hydrocarbon stream, a $C_3$-$C_4$ portion of the steam cracker recycle stream, or both to form propylene and butylene; and passing the propylene and butylene to the final separator to produce the one or more product streams.

A tenth aspect may include any one of the first through ninth aspects, further including initially passing the hydrocarbon oil stream through a feed separator to separate the hydrocarbon oil stream into at least a heavy hydrocarbon fraction, a feed middle distillate stream, and a feed naphtha stream; solvent deasphalting the heavy hydrocarbon fraction to form at least the deasphalted oil stream and the heavy residual hydrocarbons; and steam enhanced catalytically cracking at least the feed middle distillate stream in the first steam enhanced catalytic cracker to form the light steam enhanced catalytically cracked product; and processing the feed naphtha stream in the aromatics complex to produce additional benzene and xylenes.

An eleventh aspect may include any one of the first through tenth aspects, wherein the hydrocarbon oil stream includes whole crude oil or crude oil fractions.

A twelfth aspect may include any one of the sixth through eleventh aspects, wherein the solvent deasphalting unit is operated at a temperature of from 60° C. to 90° C. and a pressure of from 0.1 MPa to 0.4 MPa; the gasification unit is operated at a temperature of from 600° C. to 1100° C. and a pressure of from 1 MPa to 6.2 MPa; the hydrotreating zone is operated at a temperature of from 370° C. to 500° C. and a pressure of from 0.1 MPa to 0.2 MPa; the steam enhanced catalytic cracking system is operated at a temperature of from 525° C. to 750° C. and a pressure of from 0.1 MPa to 0.2 MPa; the methane cracking zone is operated at a temperature of from 850° C. to 1200° C. and a pressure of from 0.1 MPa to 0.2 MPa; and the steam cracking zone is operated at a temperature of from 800° C. to 950° C. and a pressure of from 0.1 MPa to 0.2 MPa.

A thirteenth aspect may include any one of the first through twelfth aspects, wherein the deasphalted oil stream includes $C_1$ to $C_{5+}$ hydrocarbons; the heavy residual hydrocarbons include $C_{5+}$ hydrocarbons having boiling points of between 426° C. to 650° C.; the syngas comprises hydrogen, carbon monoxide, carbon dioxide, or combinations thereof; and the gasification residue comprises char particles, ash, slag, tar, or combinations thereof.

A fourteenth aspect may include any one of the first through thirteenth aspects, and may include an integrated system for the conversion of hydrocarbon oil feed stocks utilizing a gasification unit, steam enhanced catalytic cracker, and an aromatics complex, including a solvent deasphalting unit configured to separate a hydrocarbon oil stream into at least a deasphalted oil stream and heavy residual hydrocarbons, the heavy residual hydrocarbons including at least asphaltenes; a gasification unit fluidly connected to the solvent deasphalting unit and configured to process the heavy residual hydrocarbons to form syngas and gasification residue; a hydrotreater fluidly connected to the solvent deasphalting unit and configured to hydrotreat at least the deasphalted oil stream to form a light $C_{5+}$ hydrocarbon stream and a heavy $C_{5+}$ hydrocarbon stream; a first steam enhanced catalytic cracker fluidly connected to the hydrotreater and configured to crack at least a portion of the light $C_{5+}$ hydrocarbon fraction to form a light steam enhanced catalytically cracked product; and a second steam enhanced catalytic cracker fluidly connected to the hydrotreater, in parallel with the first steam enhanced catalytic cracker, and configured to crack at least a portion of the heavy $C_{5+}$ hydrocarbon fraction to form a heavy steam enhanced catalytically cracked product; a product separator fluidly connected to the first and second steam enhanced catalytic crackers and configured to produce an olefin product stream, a naphtha product stream, and a BTX product stream; and an aromatics complex fluidly connected to the product separator and configured to process the naphtha product stream to produce benzene and xylenes, and wherein a ratio of gas hourly space velocity of steam to gas hourly space velocity of $C_{5+}$ hydrocarbon stream in the first and second steam enhanced catalytic crackers is from 0.1 to 1.1 times steam to $C_{5+}$ hydrocarbon stream.

A fifteenth aspect may include the fourteenth aspect, further including a catalytic reformer fluidly connected to the product separator and configured to catalytically reform the naphtha product stream to produce a reformate stream including benzene, toluene, and xylenes; and a transalkylation unit fluidly connected to the catalytic reformer and configured to upgrade the toluene in the reformate stream to produce additional benzene, xylenes, or both.

A sixteenth aspect may include the fifteenth aspect, wherein the product separator is additionally configured to produce one or more product separator recycle streams; the one or more product separator recycle streams include a methane recycle stream, a steam cracker recycle stream, a hydrotreater recycle stream, or combinations thereof; the steam cracker recycle stream includes $C_2$-$C_4$ hydrocarbons; the hydrotreater recycle stream includes cracked naphtha, light cycle oil, heavy cycle oil, or combinations thereof.

A seventeenth aspect may include the sixteenth aspect, further including a methane cracker fluidly connected to the hydrotreater and product separator and configured to crack a $C_1$ hydrocarbon stream, the methane recycle stream, or both, to form hydrogen for recycling in the hydrotreater; and a steam cracker fluidly connected to the hydrotreater and product separator and configured to crack a $C_2$-$C_4$ hydrocarbon stream, the steam cracker recycle stream, or both, to form a steam cracked product including light olefins, naphtha, and BTX for separation in the product separator; and wherein, the hydrotreater is additionally configured to form the $C_1$ hydrocarbon stream and the $C_2$-$C_4$ hydrocarbon stream; the hydrotreater is fluidly connected to the product separator and additionally configured to hydrotreat the hydrotreater recycle stream to produce additional $C_1$ hydrocarbon stream, $C_2$-$C_4$ hydrocarbon stream, light $C_{5+}$ hydrocarbon stream, heavy $C_{5+}$ hydrocarbon stream, or combinations thereof; the gasification unit is fluidly connected to the product separator and additionally configured to form additional syngas and gasification residue; and the product separator is configured to send the methane recycle stream to the methane cracker, the steam cracker recycle stream to the steam cracker, and the hydrotreater recycle stream to the hydrotreater.

An eighteenth aspect may include the seventeenth aspect, further including a catalytic reformer fluidly connected to the first and second steam enhanced catalytic crackers, and configured to catalytically reform the naphtha product stream to produce a reformate stream including benzene, toluene, and xylenes; one or more extractive distillation units are fluidly connected to the catalytic reformer, the product separator, and the hydrotreater and are configured to separate the benzene, toluene, and xylenes, produce a $C_1$-$C_4$ hydrocarbon recycle stream, and produce a $C_{9+}$ hydrocarbon stream; and a transalkylation unit fluidly connected to the one or more extractive distillation units and configured to upgrade the toluene to produce additional benzene, xylene, or both, and wherein the one or more extractive distillation units are additionally configured to send the $C_1$-$C_4$ hydrocarbon recycle stream to the product separator to produce additional methane recycle stream, additional steam cracker recycle stream, or both; and the one or more extractive distillation units are additionally configured to send the $C_{9+}$ hydrocarbon stream to the hydrotreater to produce additional $C_1$ hydrocarbon stream, $C_2$-$C_4$ hydrocarbon stream, light $C_{5+}$ hydrocarbon stream, heavy $C_{5+}$ hydrocarbon stream, or combinations thereof.

The nineteenth aspect may include the eighteenth aspect, further including a dehydrogenation unit fluidly connected to the hydrotreater and the product separator and configured to dehydrogenate a $C_3$-$C_4$ portion of the $C_2$-$C_4$ hydrocarbon stream, a $C_3$-$C_4$ portion of the steam cracker recycle stream, or both to form propylene and butylene, and wherein, the steam cracker is configured to crack a $C_2$ portion of the $C_2$-$C_4$ hydrocarbon stream, a $C_2$ portion of the steam cracker recycle stream, or both to form the steam cracked product; and the dehydrogenation unit is additionally configured to send the propylene and butylene to the product separator.

A twentieth aspect may include any one of the fifteenth through twentieth aspects, further including a feed separator fluidly connected to the solvent deasphalting unit, the first steam enhanced catalytic cracker, and the aromatics complex and configured to separate the hydrocarbon oil stream into at least a heavy oil fraction stream, a feed middle distillate stream, and a feed naphtha stream and wherein, the solvent desasphalting unit is additionally configured to separate the heavy oil fraction into at least the heavy residual hydrocarbons and the de-asphalted oil stream; the first steam enhanced catalytic cracker is additionally configured to crack the feed middle distillate stream into the light steam enhanced catalytically cracked product; and the aromatics complex is additionally configured to process the feed naphtha stream to produce additional benzene and xylenes.

A twenty-first aspect may include any one of the fifteenth through twentieth aspects, wherein the first steam enhanced catalytic cracker is additionally configured to form a olefin to naphtha ratio of from 2:1 to 7:1 olefins to naphtha; and the second steam enhanced catalytic cracker is additionally configured to form a olefin to naphtha ratio of from 1.5:1 to 0.8:1 olefins to naphtha.

A twenty-second aspect may include any one of the first through fourteenth aspect, wherein steam enhanced catalytically cracking the light $C_{5+}$ hydrocarbon stream forms the olefins and the naphtha in a ratio of from 2:1 to 7:1 olefins to naphtha; and steam enhanced catalytically cracking the heavy $C_{5+}$ hydrocarbon stream forms the olefins and the naphtha in a ratio of from 1.5:1 to 0.8:1 olefins to naphtha.

It is noted that recitations in the present disclosure of a component of the present disclosure being "operable" or "sufficient" in a particular way, to embody a particular property, or to function in a particular manner, are structural recitations, as opposed to recitations of intended use. More specifically, the references in the present disclosure to the manner in which a component is "operable" or "sufficient" denotes an existing physical condition of the component and, as such, is to be taken as a definite recitation of the structural characteristics of the component.

It is also noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

Having described the subject matter of the present disclosure in detail and by reference to specific embodiments, it is noted that the various details disclosed in the present disclosure should not be taken to imply that these details relate to elements that are essential components of the various embodiments described in the present disclosure. Further, it will be apparent that modifications and variations are possible without departing from the scope of the present disclosure, including, but not limited to, embodiments defined in the appended claims.

The singular forms "a", "an" and "the" include plural referents, unless the context clearly dictates otherwise.

Throughout this disclosure ranges are provided. It is envisioned that each discrete value encompassed by the ranges are also included. Additionally, the ranges which may be formed by each discrete value encompassed by the explicitly disclosed ranges are equally envisioned.

As used herein and in the appended claims, the words "comprise," "has," and "include" and all grammatical variations thereof are each intended to have an open, non-limiting meaning that does not exclude additional elements or steps.

As used herein, terms such as "first" and "second" are arbitrarily assigned and are merely intended to differentiate between two or more instances or components. It is to be understood that the words "first" and "second" serve no other purpose and are not part of the name or description of the component, nor do they necessarily define a relative location, position, or order of the component. Furthermore, it is to be understood that the mere use of the term "first" and "second" does not require that there be any "third" component, although that possibility is contemplated under the scope of the present disclosure.

What is claimed is:

1. An integrated process for upgrading a hydrocarbon oil feed stream, the method comprising:
    solvent deasphalting the hydrocarbon oil stream to form at least a deasphalted oil stream and heavy residual hydrocarbons, the heavy residual hydrocarbons comprising at least asphaltenes;
    processing the heavy residual hydrocarbons in a gasification unit to form syngas and gasification residue;
    hydrotreating the deasphalted oil stream to form a light $C_{5+}$ hydrocarbon stream and a heavy $C_{5+}$ hydrocarbon stream;
    steam enhanced catalytically cracking the light $C_{5+}$ hydrocarbon stream in a first steam enhanced catalytic cracker to form a light steam enhanced catalytically cracked product comprising olefins, BTX, naphtha, or combinations thereof;
    steam enhanced catalytically cracking the heavy $C_{5+}$ hydrocarbon stream in a second steam enhanced catalytic cracker to form a heavy steam enhanced catalytically cracked product comprising olefins, BTX, naphtha, or combinations thereof; and
    passing at least a portion of the light steam enhanced catalytically cracked stream, the heavy steam enhanced catalytically cracked stream, or both to a product separator to produce a olefin product stream, a naphtha product stream, and a BTX product stream;
    passing the naphtha product stream directly to an aromatics complex; and
    processing the naphtha product stream in an aromatics complex to produce benzene and xylenes, and wherein
        a first ratio of gas hourly space velocity of steam to gas hourly space velocity of light $C_{5+}$ hydrocarbon stream in the first steam enhanced catalytic cracker is less than a second ratio of gas hourly space velocity of steam to heavy $C_{5+}$ hydrocarbon stream in the second steam enhanced catalytic cracker,
        the first ratio is from 0.2 to 0.8, and
        the second ratio is from 0.8 to 1.0.

2. The process of claim 1, wherein processing the naphtha product stream in the aromatics complex further comprises:
    catalytically reforming the naphtha product stream to produce a reformate stream comprising benzene, toluene, and xylene; and
    upgrading the toluene in the reformate stream in a transalkylation unit to form additional benzene, xylenes, or both.

3. The process of claim 1, wherein
    the light $C_{5+}$ hydrocarbon fraction comprises $C_{5+}$ hydrocarbons having a $T_{95}$ boiling point of less than 200° C.; and
    the heavy $C_{5+}$ hydrocarbon fraction comprises $C_{5+}$ hydrocarbons having a $T_5$ boiling point of greater than or equal to 200° C.

4. The process of claim 1, wherein
    hydrotreating the deasphalted oil stream additionally forms a $C_1$ hydrocarbon stream and a $C_2$-$C_4$ hydrocarbon stream; and the $C_1$ hydrocarbon stream, the $C_2$-$C_4$ hydrocarbon stream, the light $C_{5+}$ hydrocarbon stream, and the heavy $C_{5+}$ hydrocarbon stream together comprise a hydrotreated product stream.

5. The process of claim 4, further comprising:
methane cracking the $C_1$ hydrocarbon stream to form hydrogen;
steam cracking the $C_2$-$C_4$ hydrocarbon stream to form a steam cracked product comprising olefins, naphtha, and BTX;
passing the steam cracked product to the product separator to thereby separate the olefins, the naphtha, and the BTX, and to thereby produce the olefin product stream, the naphtha product stream, the BTX product stream, and one or more product separator recycle streams, wherein the one or more product separator recycle streams comprise a methane recycle stream, a steam cracker recycle stream, a hydrotreater recycle stream, or combinations thereof;
hydrotreating the hydrotreater recycle stream to form additional $C_1$ hydrocarbon stream, $C_2$-$C_4$ hydrocarbon stream, light $C_{5+}$ hydrocarbon stream, heavy $C_{5+}$ hydrocarbon stream, or combinations thereof, wherein the hydrotreater recycle stream comprises cracked naphtha and light cycle oil having boiling points of between 185° C. to 650° C.;
methane cracking the methane recycle stream to form additional hydrogen;
steam cracking the steam cracker recycle stream to form additional steam cracked product, wherein the steam cracker recycle stream comprises $C_2$-$C_4$ hydrocarbons; and
passing the hydrogen to the hydrotreater to be recycled in the hydrotreater.

6. The process of claim 5, further comprising:
processing the naphtha product stream in the aromatics complex, wherein processing the naphtha product stream in the aromatics complex further comprises:
catalytically reforming the naphtha to produce a reformate stream comprising benzene, toluene, and xylene,
passing at least a portion of the reformate stream through one or more extractive distillation units to separate the benzene, toluene, and xylenes, produce a $C_1$-$C_4$ hydrocarbon recycle stream, and produce a $C_{9+}$ hydrocarbon stream, and
upgrading the toluene in a transalkylation unit to form additional benzene, xylenes, or both;
passing the $C_1$-$C_4$ hydrocarbon recycle stream to the product separator to produce additional methane recycle stream, additional steam cracker recycle stream, or both; and
passing the $C_{9+}$ hydrocarbon stream to the hydrotreater to produce additional $C_1$ hydrocarbon stream, $C_2$-$C_4$ hydrocarbon stream, light $C_{5+}$ hydrocarbon stream, heavy $C_{5+}$ hydrocarbon stream, or combinations thereof.

7. The process of claim 1, further comprising:
initially passing the hydrocarbon oil stream through a feed separator to separate the hydrocarbon oil stream into a heavy hydrocarbon fraction, a light hydrocarbon fraction, and a feed naphtha stream;
solvent deasphalting the heavy hydrocarbon fraction to form at least the deasphalted oil stream and the heavy residual hydrocarbons;
steam enhanced catalytically cracking at least the light hydrocarbon fraction in the first steam enhanced catalytic cracker to form the light steam enhanced catalytically cracked product; and
processing the feed naphtha stream in the aromatics complex to produce additional benzene and xylenes.

8. The process of claim 1, wherein the hydrocarbon oil stream comprises whole crude oil or crude oil fractions.

9. The process of claim 6, wherein:
the solvent deasphalting unit is operated at a temperature of from 60° C. to 90° C. and a pressure of from 0.1 MPa to 0.4 MPa;
the gasification unit is operated at a temperature of from 600° C. to 1100° C. and a pressure of from 1 MPa to 6.2 MPa;
the hydrotreating zone is operated at a temperature of from 370° C. to 500° C. and a pressure of from 0.1 MPa to 0.2 MPa;
the steam enhanced catalytic cracking system is operated at a temperature of from 525° C. to 750° C. and a pressure of from 0.1 MPa to 0.2 MPa;
the methane cracking zone is operated at a temperature of from 850° C. to 1200° C. and a pressure of from 0.1 MPa to 0.2 MPa;
the steam cracking zone is operated at a temperature of from 800° C. to 950° C. and a pressure of from 0.1 MPa to 0.2 MPa;
the catalytic reformer is operated at a temperature of from 450° C. to 600° C. and a pressure of from 0.7 MPa to 7 MPa; and
the transalkylation unit is operated at a temperature of from 350° C. to 450° C. and a pressure of from 1 MPa to 5 MPa.

10. The process of claim 1, wherein:
the deasphalted oil comprises $C_1$ to $C_{5+}$ hydrocarbons;
the heavy residual hydrocarbons comprise $C_{5+}$ hydrocarbons having boiling points of between 426° C. to 650° C.;
the syngas comprises hydrogen, carbon monoxide, carbon dioxide, or combinations thereof; and
the gasification residue comprises char particles, ash, slag, tar, or combinations thereof.

11. The process of claim 1, wherein:
steam enhanced catalytically cracking the light $C_{5+}$ hydrocarbon stream in the first steam enhanced catalytic cracker forms the olefins and the naphtha in a ratio of from 2:1 to 7:1 olefins to naphtha; and
steam enhanced catalytically cracking the heavy $C_{5+}$ hydrocarbon stream in the second steam enhanced catalytic cracker forms the olefins and the naphtha in a ratio of from 1.5:1 to 0.8:1 olefins to naphtha.

12. The process of claim 1, wherein processing the naphtha product stream in the aromatics complex does not comprise hydrotreating and further comprises:
catalytically reforming the naphtha product stream to produce a reformate stream comprising benzene, toluene, and xylene; and
upgrading the toluene in the reformate stream in a transalkylation unit to form additional benzene, xylenes, or both.

* * * * *